United States Patent [19]

Böshagen et al.

[11] Patent Number: 4,940,705

[45] Date of Patent: Jul. 10, 1990

[54] N-SUBSTITUTED DERIVATIVES OF 1-DESOXYNOJIRIMYCIN AND 1-DESOXYMANNONOJIRIMYCIN AND PHARMACEUTICAL USE

[75] Inventors: Horst Böshagen, Haan; Bodo Junge, Wuppertal; Arnold Paessens, Haan; Matthias Schüller, Wuppertal, all of Fed. Rep. of Germany

[73] Assignee: Bayer Aktiengesellschaft, Leverkusen, Fed. Rep. of Germany

[21] Appl. No.: 262,902

[22] Filed: Oct. 26, 1988

[30] Foreign Application Priority Data

Oct. 30, 1987 [DE] Fed. Rep. of Germany ....... 3736771
Apr. 29, 1988 [DE] Fed. Rep. of Germany ....... 3814549

[51] Int. Cl.$^5$ ................. A61K 31/445; C07C 211/46
[52] U.S. Cl. ............... 514/227.8; 514/235.5;
514/235.8; 514/255; 514/256; 514/305;
514/314; 514/315; 514/316; 514/318; 514/321;
514/326; 514/328; 544/58.4; 544/58.6;
544/122; 544/130; 544/238; 544/245; 544/335;
544/360; 546/133; 546/165; 546/173; 546/188;
546/193; 546/194; 546/197; 546/201; 546/206;
546/208; 546/213; 546/214; 546/242

[58] Field of Search ............... 546/133, 165, 173, 188,
546/193, 194, 197, 201, 206, 208, 213, 214, 242;
544/58.4, 58.6, 122, 130, 238, 245, 335, 360;
514/227.8, 235.5, 235.8, 255, 256, 305, 315, 314,
316, 318, 321, 326, 328

[56] References Cited

FOREIGN PATENT DOCUMENTS 0193770 9/1986 European Pat. Off. .

OTHER PUBLICATIONS

Chemical Abstracts, Band 107, No. 25, 21. Dec. 1987, Seite 27, No. 228527r, Columbus, Ohio, US; P. S. Sunkara et al.: "Antiretroviral Activity of Castanospermine and Deoxynojirimycin, Specific Inhibitors of Glyco-protein Processing", & Biochem. Biophys. Res. Commun., 1987, 148(1), 206–10 *Zusammenfassung*.
Chemical Abstracts, Band 100, No. 1, 1984, Seite 293, No. 3381u, Columbus, Ohio, US; P. A. Romero et al.: "N-Methyl-1-Deoxynojirimycin, A Novel Inhibitor of Glycoprotein Processing, and its Effect on Fowl Plague Virus Maturation", & Virogoly, 1983, 130(1). 238–242 *Zusammenfassung*.

Primary Examiner—Richard L. Raymond
Attorney, Agent, or Firm—Sprung Horn Kramer & Woods

[57] ABSTRACT

N-substituted derivatives of 1-desoxynojirimycin and 1-desoxymannonojirimycin of the formula

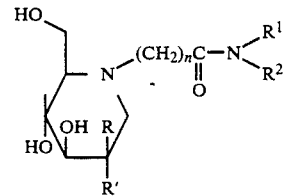

in which
one of R and R' are hydroxyl and the other is hydrogen
n is a number from 1 to 6
$R^1$ is hydrogen, alkyl or benzyl and
$R^2$ is alkyl which is optionally substituted by an optionally substituted aryl or by pyridyl, thienyl, furyl, pyrimidyl, pyrazinyl or quinolyl or $R_1$ is cycloalkyl or $R^2$ is optionally substituted by aryl or $R^2$ is a saturated bridged heterocycle or $R^1$ and $R^2$ together can form a heterocyclic ring which is optionally substituted. These compounds are useful in the treatment of and prophylaxis of viral infections.

9 Claims, No Drawings

N-SUBSTITUTED DERIVATIVES OF 1-DESOXYNOJIRIMYCIN AND 1-DESOXYMANNONOJIRIMYCIN AND PHARMACEUTICAL USE

The invention relates to N-substituted derivatives of 1-desoxynojirimycin and 1-desoxymannonojirimycin, processes for their preparation and their use in medicaments, in particular in antiviral medicaments.

It has been disclosed that derivatives of 1-desoxynojirimycin and 1-desoxymannonojirimycin are glucosidase inhibitors and can be employed for the treatment of disorders of carbohydrate metabolism [EP 947; EP 8,058; EP 34,784; EP 2,848,117; EP 193,770]. Moreover, it is known that certain 1-desoxynojirimycin derivatives exhibit herbicidal properties [DE 3,024,901] and 1-desoxynojirimycin and 1-desoxymannonojirimycin and derivatives thereof influence the biosynthesis of glycoproteins [U. Fuhrmann, E. Bause and H. Ploegh; Review: Biochimica et Biophysica Acta 825, 95–110 (1985)].

The present invention relates to N-substituted derivatives of 1-desoxynojirimycin and 1-desoxymannonojirimycin of the general formula (I)

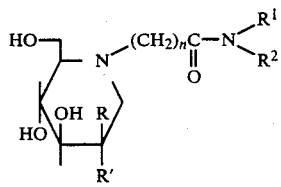

in which

R or R' stands for a hydroxyl group and in which the other R' or R in each case stands for hydrogen, n stands for a number from 1 to 6, $R^1$ stands for hydrogen, or stands for straight-chain or branched alkyl having up to 3 carbon atoms or for benzyl, and $R^2$
stands for straight-chain or branched alkyl having up to 8 carbon atoms, which can be substituted by aryl having 6 to 10 carbon atoms, where the aryl radical can carry up to 4 identical or different substituents from the series comprising fluorine, chlorine, bromine, iodine, cyano, nitro, alkyl, alkoxy, alkylthio or arylthio each having up to 6 carbon atoms, dioxymethylene, dioxyethylene, trifluoromethyl, trifluoromethoxy, difluoromethoxy, carboxyl or alkoxycarbonyl having up to 4 carbon atoms, or which can be substituted by pyridyl, thienyl, furyl, pyrimidyl, pyridazinyl, pyrazinyl or quinolyl, or stands for cycloalkyl having 3 to 7 carbon atoms, or stands for aryl having 6 to 10 carbon atoms, where the aryl radical can be monosubstituted to tetrasubstituted by fluorine, chlorine, bromine, iodine, cyano, alkyl having up to 6 carbon atoms, alkoxy having up to 12 carbon atoms, alkylsulphonyl having up to 4 carbon atoms, trifluoromethyl, trifluoromethoxy, difluoromethylene, difluoromethoxy, trifluoromethylthio, dioxymethylene, dioxyethylene, by cycloalkyl having 3 to 7 carbon atoms, by carboxyl or alkoxycarbonyl having up to 4 carbon atoms, by aryloxy having 6 to 10 carbon atoms, where the aryl radical can carry up to 4 identical or different substituents from the series comprising fluorine, chlorine, bromine, iodine, cyano, hydroxyl, nitro, alkyl, alkoxy, alkylthio having up to 6 carbon atoms, dioxymethylene, dioxyethylene, trifluoromethyl, trifluoromethoxy or difluoromethoxy, or by halogenoalkoxy having up to 6 carbon atoms and up to 5 fluorine and/or 3 chlorine atoms, or by hydroxyalkoxy, hydroxyalkyl or cyanoalkyl each having up to 8 carbon atoms, or by alkenyloxy having up to 6 carbon atoms, or by a group $-XR^3$, the substituents being identical or different, where X denotes a straight-chain or branched alkylene or alkenylene chain having up to 8 carbon atoms, and $R^3$ denotes aryl having 6 to 10 carbon atoms, where the aryl radical can carry up to 4 identical or different substituents from the series comprising fluorine, chlorine, bromine, iodine, cyano, alkyl, alkoxy, alkylthio each having up to 6 carbon atoms, nitro, dioxymethylene, dioxyethylene, trifluoromethyl, trifluoromethoxy, difluoromethoxy or trofluoromethylthio, or denotes a 5- to 6-membered saturated or unsaturated heterocyclic ring which can be fused to benzene and which can contain oxygen, sulphur or up to 2 nitrogen atoms as hetero atoms, or denotes hydroxyl, carboxyl, alkoxycarbonyl having up to 6 carbon atoms, alkylcarbonyloxy having up to 18 carbon atoms, cycloalkyl having 3 to 6 carbon atoms, or denotes a group $-OSO_3H$, $-CONH-NH_2$, $-CONH_2$ or amino, alkylamino or dialkylamino each having up to 6 carbon atoms per alkyl group, or denotes alkyl or hydroxyalkyl having up to 8 carbon atoms, or denotes a saturated, bridged heterocycle or $R^1$ and $R^2$, together with the nitrogen atom, form a 5- to 6-membered ring which can be anellated, which can be interrupted by oxygen, sulphur or the group $-NR^4$, and which can be substituted by alkyl having up to 4 carbon atoms, hydroxyl, phenyl, carboxyl or alkoxycarbonyl having up to 4 carbon atoms, where $R^4$ denotes aryl having 6 to 10 carbon atoms, where the aryl radical can carry up to 4 identical or different substituents from the group comprising fluorine, chlorine, bromine, iodine, cyano, nitro, hydroxyl, alkyl, alkoxy, alkylthio having up to 6 carbon atoms, dioxymethylene, dioxyethylene, trifluoromethyl, trifluoromethoxy or difluoromethoxy, or denotes alkoxycarbonyl having up to 6 carbon atoms, or denotes pyridyl, pyrimidyl, furyl, thienyl, pyrazinyl, pyridazinyl or quinolyl, or denotes cycloalkyl having 3 to 7 carbon atoms, or denotes alkyl or alkenyl having up to 6 carbon atoms which can be monosubstituted or disubstituted by phenyl which is optionally substituted by chlorine, dioxymethylene or trifluoromethyl, hydroxyl, amino, alkylamino, dialkylamino each having up to 3 carbon atoms per alkyl group, fluorine, chlorine, bromine, cycloalkyl having 3 to 6 carbon atoms, by carboxyl or alkoxycarbonyl having up to 6 carbon atoms, by pyridyl, pyrimidyl, pyrazinyl, morpholinyl, thiomorpholinyl, pyrrolidinyl or pyrrolidinocarbonyl, by morpholinocarbonyl, by alkylaminocarbonyl, dialkylaminocarbonyl or phenylalkylaminocarbonyl each having up to 6 carbon atoms per alkyl group, the substituents being identical or different.

Preferred compounds of the general formula (I) which may be mentioned are those in which
n stands for the numbers 1 to 4,
$R^1$ stands for hydrogen, and
$R^2$
stands for straight-chain or branched alkyl having up to 6 carbon atoms, which can be substituted by pyridyl, thienyl or by phenyl, where the phenyl radical can carry up to 3 identical or different substituents from the series comprising fluorine, chlorine, bromine, hydroxyl, alkyl, alkoxy having up to 4 carbon atoms, dioxymethylene, dioxyethylene or carboxyl, or
stands for cyclopentyl, cyclohexyl or cycloheptyl, or
stands for quinuclidine or
stands for 1,2,3,4-tetrahydroisoquinoline, or
stands for phenyl which can be monosubstituted, disubstituted or trisubstituted by fluorine, chlorine, bromine, cyano, alkyl having up to 4 carbon atoms, hydroxyalkyl or hydroxyalkoxy having up to 4 carbon atoms, trifluoromethyl, trifluoromethoxy, dioxymethylene, dioxyethylene, by phenyl which is optionally substituted in the aromatic part by fluorine, chlorine, bromine, hydroxyl, alkyl, alkoxy having up to 9 carbon atoms, dioxymethylene, trifluoromethyl or carboxyl, or by straight-chain or branched alkenyloxy having up to 4 carbon atoms, or by a group —$XR^3$, the substituents being identical or different,
where
X denotes a straight-chain or branched alkylene chain having up to 6 carbon atoms and
$R^3$
denotes phenyl which is monosubstituted, disubstituted or trisubstituted by fluorine, chlorine, bromine, hydroxyl, alkyl, alkoxy having up to 4 carbon atoms, dioxymethylene, trifluoromethyl or carboxyl, the substituents being identical or different, or
denotes pyridyl, morpholinyl or piperidinyl, or
denotes hydroxyl, carboxyl, alkoxycarbonyl having up to 4 carbon atoms, or cyclopropyl, cyclopentyl or cyclohexyl or
denotes amino, alkylamino or dialkylamino each having up to 4 carbon atoms per alkyl group, or
$R^1$ and $R^2$, together with the nitrogen, form a ring of the formula

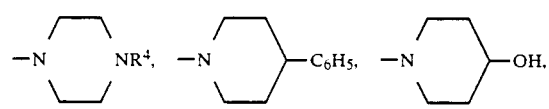

-continued

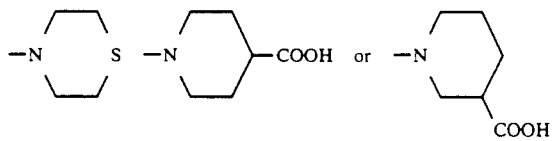

where
$R^4$
denotes phenyl which is optionally monosubstituted, disubstituted or trisubstituted by fluorine, chlorine, bromine, hydroxyl, alkyl, alkoxy having up to 4 carbon atoms, dioxymethylene, trifluoromethyl or carboxyl, the substituents being identical or different, or
denotes alkoxycarbonyl having up to 4 carbon atoms, or
denotes pyridyl or pyrimidyl, or
denotes cyclopropyl, cyclopentyl or cyclohexyl, or
denotes straight-chain or branched alkyl or alkenyl having up to 4 carbon atoms, which can be monosubstituted or disubstituted by phenyl which is optionally substituted by chlorine, trifluoromethyl or dioxymethylene, by hydroxyl, amino, methylamino, dimethylamino, fluorine, chlorine, cyclopropyl, cyclopentyl, cyclohexyl or alkoxycarbonyl having up to 4 carbon atoms, by morpholinyl, pyrrolidinyl or pyrrolidinocarbonyl, or by morpholinocarbonyl, dialkylamino or phenylalkylamino each having up to 4 carbon atoms, the substituents being identical or different.

Particularly preferred compounds of the general formula (I) which may be mentioned are those in which
n stands for the number 2,
$R^1$ stands for hydrogen, and
$R^2$
stands for straight-chain or branched alkyl having up to 3 carbon atoms, which can be substituted by thienyl or phenyl,
stands for phenyl which can be monosubstituted, disubstituted or trisubstituted by fluorine, chlorine, bromine, cyano, alkyl having up to 4 carbon atoms, hydroxyalkyl having up to 6 carbon atoms, alkoxy having up to 9 carbon atoms, hydroxyalkoxy having up to 4 carbon atoms, alkylthio having up to 4 carbon atoms, trifluoromethyl or trifluoromethoxy, the substituents being identical or different, or
stands for quinuclidinyl or
stands for 1,2,3,4-tetrahydroisoquinoline or
$R^1$ and $R^2$, together with the nitrogen, form a ring of the formula

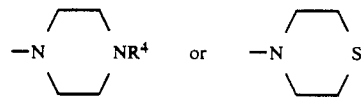

where
$R^4$
denotes phenyl which is optionally mono-substituted or disubstituted by fluorine, chlorine, bromine, hydroxyl, alkyl or alkoxy having up to 4 carbon atoms, the substituents being identical or different, or denotes alkoxycarbonyl having up to 4 carbon atoms, or denotes cyclopropyl, cyclopentyl or cyclohexyl, or denotes straight-chain or branched alkyl or alkenyl having up to 4 carbon atoms, which can be monosubstituted or disubstituted by phenyl which is optionally substituted by chlorine, trifluoromethyl or dioxymethylene, by hydroxyl, amino, dimethylamino, cyclopropyl or alkoxycarbonyl having up to 4 carbon atoms, by morpholinyl, pyrrolidinyl or pyrrolidinocarbonyl, the substituents being identical or different.

The following compounds may be mentioned as very particularly preferred:

N-(4-methoxyphenyl)-3-(1,5-didesoxy-1,5-imino-D-glucit-N-yl)propionamide,
N-(4-methoxycarbonylphenyl)-3-(1,5-didesoxy-1,5-imino-D-glucit-N-yl)propionamide,
N-[4-(4-pyridylmethoxyphenyl)]-3-(1,5-didesoxy-1,5-imino-D-glucit-N-yl)propionamide,
N-(4-benzyloxyphenyl)-3-(1,5-didesoxy-1,5-imino-D-glucit-N-yl)propionamide,
N-(4-trifluoromethoxyphenyl)-3-(1,5-didesoxy-1,5-imino-D-glucit-N-yl)propionamide,
N-(4-oxocyclohexyloxyphenyl)-3-(1,5-didesoxy-1,5-imino-D-glucit-N-yl)propionamide,
N-(4-tert.-butylphenyl)-3-(1,5-didesoxy-1,5-imino-D-glucit-N-yl)propionamide,
N-[4-(6-methylheptyloxy)phenyl]-3-(1,5-didesoxy-1,5-imino-D-glucit-N-yl)propionamide,
N-[4-(2-N,N-diethylaminoethoxy)phenyl]-3-(1,5-didesoxy-1,5-imino-D-glucit-N-yl)propionamide,
N-(4-allyloxyphenyl)-3-(1,5-didesoxy-1,5-imino-D-glucit-N-yl)propionamide,
N-(4-trifluoromethylphenyl)-3-(1,5-didesoxy-1,5-imino-D-glucit-N-yl)propionamide,
N-[4-(2-chloro-1,1,2-trifluoroethoxy)phenyl]-3-(1,5-didesoxy-1,5-imino-D-glucit-N-yl)propionamide,
N-(4-hydroxyphenyl)-3-(1,5-didesoxy-1,5-imino-D-glucit-N-yl)propionamide,
N-(4-isopropylphenyl)-3-(1,5-didesoxy-1,5-imino-D-glucit-N-yl)propionamide,
N-(2-isopropylphenyl)-3-(1,5-didesoxy-1,5-imino-D-glucit-N-yl)propionamide,
N-(4-fluorophenyl)-3-(1,5-didesoxy-1,5-imino-D-glucit-N-yl)propionamide,
N-(2-fluorophenyl)-3-(1,5-didesoxy-1,5-imino-D-glucit-N-yl)propionamide,
1-[3-(1,5-didesoxy-1,5-imino-D-glucit-N-yl)-propionyl]-2,3-dihydroindole,
N-(2,4-difluorophenyl)-3-(1,5-didesoxy-1,5-imino-D-glucit-N-yl)propionamide,
N-(2-trifluoromethylphenyl)-3-(1,5-didesoxy-1,5-imino-D-glucit-N-yl)propionamide,
N-(2,6-difluorophenyl)-3-(1,5-didesoxy-1,5-imino-D-glucit-N-yl)propionamide,
N-(adamantan-1-yl)-3-(1,5-didesoxy-1,5-imino-D-glucit-N-yl)propionamide,
N-(3,4,5-trimethoxyphenyl)-3-(1,5-didesoxy-1,5-imino-D-glucit-N-yl)propionamide,
N-(3,4-dimethoxyphenyl)-3-(1,5-didesoxy-1,5-imino-D-glucit-N-yl)propionamide,
N-(3,5-dimethoxyphenyl)-3-(1,5-didesoxy-1,5-imino-D-glucit-N-yl)propionamide,
N-(2,4,6-tribromophenyl)-3-(1,5-didesoxy-1,5-imino-D-glucit-N-yl)propionamide,
N-(3-cyanophenyl)-3-(1,5-didesoxy-1,5-imino-D-glucit-N-yl)propionamide,
N-(4-cyclohexylphenyl)-3-(1,5-didesoxy-1,5-imino-D-glucit-N-yl)propionamide,
N-(3,4-ethylenedioxyphenyl)-3-(1,5-didesoxy-1,5-imino-D-glucit-N-yl)propionamide,
N-(2-bromophenyl)-3-(1,5-didesoxy-1,5-imino-D-glucit-N-yl)propionamide,
N-(3,4-methylenedioxyphenyl)-3-(1,5-didesoxy-1,5-imino-D-glucit-N-yl)propionamide,
N-(2-methylthiophenyl)-3-(1,5-didesoxy-1,5-imino-D-glucit-N-yl)propionamide,
3-(1,5-didesoxy-1,5-imino-D-glucit-N-yl)-propionyl-4-(4-trifluoromethylphenyl)piperazine,
N-phenyl-3-(1,5-didesoxy-1,5-imino-D-glucit-N-yl)propionamide,
N-(4-ethoxyphenyl)-3-(1,5-didesoxy-1,5-imino-D-glucit-N-yl)propionamide,
N-(2-dimethylaminoethyl)-3-(1,5-didesoxy-1,5-imino-D-glucit-N-yl)propionamide,
N-[2-(3-methoxyphenyl)ethyl]-3-(1,5-didesoxy-1,5-imino-D-glucit-N-yl)propionamide,
N-(2-pyridylmethyl)-3-(1,5-didesoxy-1,5-imino-D-glucit-N-yl)propionamide,
3-(1,5-didesoxy-1,5-imino-D-glucit-N-yl)-propionyl-(4-cinnamyl)piperazine,
N-[4-(2-hydroxyethoxy)phenyl]-3-(1,5-didesoxy-1,5-imino-D-glucit-N-yl)propionamide,
N-(4-methoxyphenyl)-3-(1,5-didesoxy-1,5-imino-D-mannit-N-yl)propionamide,
N-(4-methoxycarbonylphenyl)-3-(1,5-didesoxy-1,5-imino-D-mannit-N-yl)propionamide,
N-[4-(4-pyridylmethoxy)phenyl]-3-(1,5-didesoxy-1,5-imino-D-mannit-N-yl)propionamide,
N-(4-benzyloxyphenyl)-3-(1,5-didesoxy-1,5-imino-D-mannit-N-yl)propionamide,
N-(4-trifluoromethoxyphenyl)-3-(1,5-didesoxy-1,5-imino-D-mannit-N-yl)propionamide,
N-[4-(2-oxocyclohexyloxy)phenyl]-3-(1,5-didesoxy-1,5-imino-D-mannit-N-yl)propionamide,
N-(4-tert.-butylphenyl)-3-(1,5-didesoxy-1,5-imino-D--mannit-N-yl)propionamide,
N-[4-(6-methylheptyloxy)phenyl]-3-(1,5-didesoxy-1,5-imino-D-mannit-N-yl)propionamide,
N-[4-(2-N,N-diethylaminoethoxy)phenyl]-3-(1,5-didesoxy-1,5-imino-D-mannit-N-yl)propionamide,
N-(4-allyloxyphenyl)-3-(1,5-didesoxy-1,5-imino-D-mannit-N-yl)propionamide,
N-(4-trifluoromethylphenyl)-3-(1,5-didesoxy-1,5-imino-D-mannit-N-yl)propionamide,
N-[4-(2-chloro-1,1,2-trifluoroethoxy)phenyl]-3-(1,5-didesoxy-1,5-imino-D-mannit-N-yl)propionamide,
N-(4-isopropylphenyl)-3-(1,5-didesoxy-1,5-imino-D-mannit-N-yl)propionamide,
N-(2-isopropylphenyl)-3-(1,5-didesoxy-1,5-imino-D-mannit-N-yl)propionamide,
N-(4-fluorophenyl)-3-(1,5-didesoxy-1,5-imino-D-mannit-N-yl)propionamide,
N-(2-fluorophenyl)-3-(1,5-didesoxy-1,5-imino-D-mannit-N-yl)propionamide,
1-[3-(1,5-didesoxy-1,5-imino-D-mannit-N-yl)-propionyl]2,3-dihydroindole,
N-(2,4-difluorophenyl)-3-(1,5-didesoxy-1,5-imino-D-mannit-N-yl)propionamide,
N-(2-trifluoromethylphenyl)-3-(1,5-didesoxy-1,5-imino-D-mannit-N-yl)propionamide,
N-(2,6-difluorophenyl)-3-(1,5-didesoxy-1,5-imino-D-mannit-N-yl)propionamide, N-(adamantan-1-yl)-3-(1,5-didesoxy-1,5-imino-D-mannit-N-yl)propionamide,
N-(3,4,5-trimethoxyphenyl)-3-(1,5-didesoxy-1,5-imino-D-mannit-N-yl)propionamide,
N-(3,4-dimethoxyphenyl)-3-(1,5-didesoxy-1,5-imino-D-mannit-N-yl)propionamide,
N-(3,5-dimethoxyphenyl)-3-(1,5-didesoxy-1,5-imino-D-mannit-N-yl)propionamide,
N-(2,4,6-tribromophenyl)-3-(1,5-didesoxy-1,5-imino-D-mannit-N-yl)propionamide,
N-(3-cyanophenyl)-3-(1,5-didesoxy-1,5-imino-D-mannit-N-yl)propionamide,
N-(4-cyclohexylphenyl)-3-(1,5-didesoxy-1,5-imino-D-mannit-N-yl)propionamide,
N-(3,4-ethylenedioxyphenyl)-3-(1,5-didesoxy-1,5-imino-D-mannit-N-yl)propionamide,
N-(2-bromophenyl)-3-(1,5-didesoxy-1,5-imino-D-mannit-N-yl)propionamide,
N-(3,4-methylenedioxyphenyl)-3-(1,5-didesoxy-1,5-imino-D-mannit-N-yl)propionamide,
N-(2-methylthiophenyl)-3-(1,5-didesoxy-1,5-imino-D-mannit-N-yl)propionamide,
3-(1,5-Didesoxy-1,5-imino-D-mannit-N-yl)-propionyl-4-(4-trifluoromethylphenyl)piperazine,
N-phenyl-3-(1,5-didesoxy-1,5-imino-D-mannit-N-yl)propionamide,
N-(4-ethoxyphenyl)-3-(1,5-didesoxy-1,5-imino-D-mannit-N-yl)propionamide,
N-(2-dimethylaminoethyl)-3-(1,5-didesoxy-1,5-imino-D-mannit-N-yl)propionamide,
N-[2-(3-methoxyphenyl)ethyl]-3-(1,5-didesoxy-1,5-imino-D-mannit-N-yl)propionamide,
N-(2-pyridylmethyl)-3-(1,5-didesoxy-1,5-imino-D-mannit-N-yl)propionamide,
3-(1,5-didesoxy-1,5-imino-D-mannit-N-yl)-propionyl-(4-cinnamyl)piperazine,
N-[4-(2-hydroxyethoxy)phenyl]-3-(1,5-didesoxy-1,5-imino-D-mannit-N-yl)propionamide
3-(1,5-didesoxy-1,5-imino-D-mannit-N-yl-propionyl-1-(4-p-fluorophenyl)piperazine,
3-(1,5-didesoxy-1,5-imino-D-mannit-N-yl)propionitrile,
3-(1,5-didesoxy-1,5-imino-D-mannit-N-yl)propionic acid,
3-(1,5-didesoxy-1,5-imino-D-mannit-N-yl)propionyl-1-(4-phenyl)piperazine,
3-(1,5-didesoxy-1,5-imino-D-mannit-N-yl)propionyl-1-(4-phenyl)piperazine,
3-(1,5-didesoxy-1,5-imino-D-glucit-N-yl)-propionyl-1-(4-cyclopropyl)piperazine,
N-(4-trifluoromethylbenzyl)-3-(1,5-imino-D-glucit-N-yl)propionamide,
N-(2-phenyl-2-ketoethyl)-3-(1,5-didesoxy-1,5-imino-D-glucit-N-yl)propionamide,
3-(1,5-didesoxy-1,5-imino-D-glucit-N-yl)-propionyl-1-(4-2-fluorophenyl)piperazine,
3-(1,5-didesoxy-1,5-imino-D-glucit-N-yl)propionyl-1-(4-nitrophenyl)piperazine,
3-(1,5-didesoxy-1,5-imino-D-glucit-N-yl)propionyl-1-(4-cyanophenyl)piperazine,
3-(1,5-didesoxy-1,5-imino-D-glucit-N-yl)propionyl-1-(4-methylphenyl)piperazine,
3-(1,5-didesoxy-1,5-imino-D-glucit-N-yl)propionyl-1-(4-[3-trifluoromethyl-4-chlorophenyl])piperazine,
3-(1,5-didesoxy-1,5-imino-D-glucit-N-yl)propionyl-1-(4-[2-morpholino-2-ketoethyl])piperazine,
3-(1,5-didesoxy-1,5-imino-D-glucit-N-ylpropionyl-1-(4-[2-pyrimidyl])piperazine,
3-(1,5-didesoxy-1,5-imino-D-glucit-N-yl)propionyl-1-thiomorpholide,
N-[(thiophen-2-yl)-methyl]-3-(1,5-didesoxy-1,5-imino-D-glucit-N-yl)propionamide,
N-[(1S)-1-phenethyl]-3-(1,5-didesoxy-1,5-imino-D-glucit-N-yl)propionamide,
N-[(1R)-phenethyl)]-3-(1,5-didesoxy-1,5-imino-D-glucit-N-yl)propionamide,
N-butyl-3-(1,5-didesoxy-1,5-imino-D-glucit-N-yl)-propionamide,
N-t-butyl-3-(1,5-didesoxy-1,5-imino-D-glucit-N-yl)-propionamide,
N-(4-decyloxyphenyl)-3-(1,5-didesoxy-1,5-imino-D-glucit-N-yl)propionamide,
N-(4-ethoxyphenyl)-4-(1,5-didesoxy-1,5-imino-D-glucit-N-yl)butanamide,
N-(4-t-butylphenyl)-4-(1,5-didesoxy-1,5-imino-D-glucit-N-yl)butanamide,
N-[4-(2-chloro-1,1,2-trifluoroethoxy)phenyl]-4-(1,5-didesoxy-1,5-imino-D-glucit-N-yl)butanamide,
N-(4-cyclohexylphenyl)-4-(1,5-didesoxy-1,5-imino-D-glucit-N-yl)butanamide,
1-[3-(1,5-didesoxy-1,5-imino-D-glucit-N-yl)propionyl]-1,2,3,4-tetrahydroquinoline.

In the context of investigations which led to the present invention, it was surprisingly found that the compounds of the general formula (I) according to the invention possess an exceedingly good action against retroviruses.

The compounds according to the invention can be prepared by reacting carboxylic acids of the general formula (II)

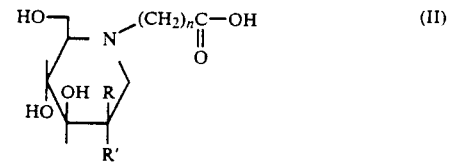

in which n has the abovementioned meaning, by known methods, if appropriate, via a reactive acid derivative, with amines of the general formula (III)

in which $R^1$ and $R^2$ have the abovementioned meaning, if appropriate in the presence of an inert organic solvent.

Reactive acid derivatives which may be mentioned, for example, are: activated esters, hydroxysuccinimide esters, acid imidazolides, acid halides, mixed anhydrides, or the reaction in the presence of carbodiimides, such as, for example cyclohexylcarbodiimide.

The process according to the invention can be illustrated, for example, by the following equation:

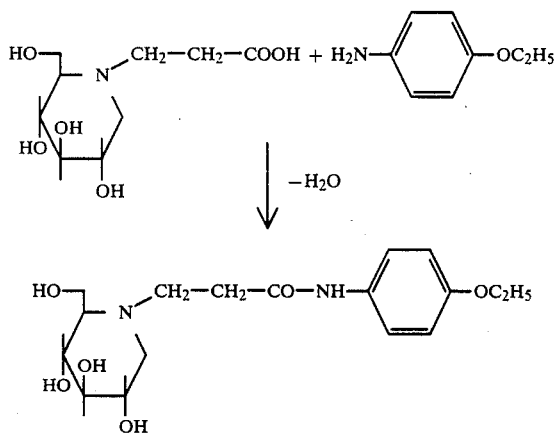

Carrying out the process according to the invention relies on the method known in the literature for the conversion of carboxylic acids into carboxamides. Thus, the carboxylic acid is first converted into an activated form, such as, for example, the acid chloride or the imidazolide, which are either isolated as such and reacted in a second reaction step, or which are amidated directly to the compounds according to the invention in situ. As activating reagents, carbodiimides such as dicyclohexylcarbodiimide or 1-cyclohexyl-3-[2-(N-methylmorpholino)ethyl]carbodiimide-p-toluenesulphonates or N-hydroxyphthalimide or N-hydroxy-benzotriazole in the presence of dicyclohexylcarbodiimide may be mentioned, for example, in addition to the inorganic halides such as thionyl chloride, phosphorus trichloride or phosphorus pentachloride, or carbonyldiimidazole. Naturally, piperidin-N-yl carboxylic acids can also be employed in the form of their salts. [The method of amidation is described, for example, in: Fieser & Fieser, Reagents for Organic Synthesis, John Wiley & Sons Inc. (1967), pages 231–236; J. C. Shihan and G. P. Hess, J. Am. Chem. Soc. 77, 1067 (1955); U. Goodman, G. W. Kenner, Adv. in Protein Chem. 12, 488 (1957); W. A. Bonner, P. I. McNamee, J. Org. Chem. 26, 254 (1961); H. A. Staab, Angew. Chemie Int. Ed. 1, 351 (1962); Fieser & Fieser, Reagents for Organic Synthesis, John Wiley & Sons Inc. 1967, 116, 114; H. C. Beyerman, U. O. van der Brink, Re. Trav. 80, 1372 (1961); C. A. Buehler and D. E. Pearson, John Wiley & Sons, Volume I (1970), page 895 ff, Volume II (1977)].

Suitable solvents for the process according to the invention are, in addition to water, all inert organic solvents which are not changed under the reaction conditions. These preferably include ethers such as diethylether, dioxane, tetrahydrofuran, glycol monomethyl ether or glycol dimethyl ether or halogenated hydrocarbons such as dichloromethane, trichloromethane or tetrachloromethane, or amides such as dimethylformamide, dimethylacetamide or hexamethylphosphoric triamide, or hydrocarbons such as benzene, toluene or xylene, or acetonitrile, nitromethane, pyridine, dimethyl sulphoxide or ethyl acetate. Mixtures of the solvents mentioned can also be used.

The reaction temperatures can be varied within a wide range. In general, the reaction is carried out in a range from $-70°$ C. to $+140°$ C., preferably from $-20°$ C. to $+100°$ C.

The reaction can be carried out at normal pressure, but also at elevated or reduced pressure. In general, the reaction is carried out at normal pressure.

When carrying out the process according to the invention, the ratio of the substances participating in the reaction is arbitrary. In general, the reaction is carried out with molar amounts of reactants. However, it has proved favorable to employ the amine in a 5 to 10-fold molar excess. The use of the amine in a large excess directly as the solvent is particularly expedient.

The D-gluco configuration carboxylic acids of 1-desoxynojirimycin employed as starting materials are known [DE 3,024,901; DE 2,758,025; DE 2,922,760; JP 81/103,153].

The D-manno configuration carboxylic acids of 1-desoxynojirimycin employed as starting materials and their preparation are new.

Carboxylic acids which are used, for example, according to the invention are:
N-[2-carboxyethyl]-1-desoxynojirimycin,
N-[3-carboxypropyl]-1-desoxynojirimycin,
N-[4-carboxybutyl]-1-desoxynojirimycin,
N-[2-carboxyethyl]-1-desoxymannonojirimycin,
N-[3-carboxypropyl]-1-desoxymannonojirimycin or
N-[4-carboxybutyl]-1-desoxymannonojirimycin.

The amines employed as starting materials are known or can be prepared by known methods, such as are described, for example, in Beilstein's Handbuch der Organischen Chemie (Beilstein's Handbook of Organic Chemistry).

Amines which are used, for example, according to the invention are:
2-fluoroaniline,
4-fluoroaniline,
2-bromoaniline,
4-iodoaniline,
2-trifluoromethylaniline,
4-hydroxyaniline,
3-trifluoromethylaniline,
4-trifluoromethylaniline,
3-cyanoaniline,
2-methylmercaptoaniline,
3,4-methylenedioxyaniline,
3,4-ethylenedioxyaniline,
3,4-dimethoxyaniline,
3,5-dimethoxyaniline,
3,4,5-trimethoxyaniline,
2,6-difluoroaniline,
2,4-difluoroaniline,
3,4-difluoroaniline,
2,4,6-tribromoaniline,
2-isopropylaniline,
4-isopropylaniline,
4-(t-butyl)aniline,
4-cyclohexylaniline,
2,3-dihydroindole,
1,2,3,4-tetrahydroisoquinoline,
thiomorpholine
2,2-dimethyl-1-propylamine,
2-ethylbutylamine,
cyclopentylamine,
cycloheptylamine,
1-phenylpiperazine,
1-(2-methylphenyl)piperazine,
1-(3-methylphenyl)piperazine,
1-(4-methylphenyl)piperazine,
1-(2-ethylphenyl)piperazine,
1-(2-chlorophenyl)piperazine, 1-(3-chlorophenyl)piperazine,
1-(2-fluorophenyl)piperazine,
1-(4-fluorophenyl)piperazine,
1-(2-cyanophenyl)piperazine,
1-(2-nitrophenyl)piperazine,
1-(4-nitrophenyl)piperazine,
1-(2-methoxyphenyl)piperazine,
1-(3-methoxyphenyl)piperazine,
1-(4-methoxyphenyl)piperazine,
1-(2-ethoxyphenyl)piperazine,
1-(2-methylmercaptophenyl)piperazine,
1-(2-hydroxphenyl)piperazine,
1-(4-hydroxyphenyl)piperazine,
1-(4-trifluoromethylphenyl)piperazine,
1-(3-trifluoromethylphenyl)piperazine,
1-(3-trifluorometyl-4-chlorophenyl)piperazine,
1-(2,3-dimethylphenyl)piperazine,
1-(2,6-dimethylphenyl)piperazine,
1-(3,4-dimethylphenyl)piperazine,
1-(3,5-dichlorophenyl)piperazine,
1-(3,4-methylenedioxyphenyl)piperazine,
1-(2,4-dimethoxyphenyl)piperazine,
1-(3,4-dimethoxyphenyl)piperazine,
1-(3,5-dimethoxyphenyl)piperazine,
1-(3,4,5-trimethoxyphenyl)piperazine,
1-(2-pyridyl)piperazine,
1-(4-pyridyl)piperazine,
1-(2-pyrimidyl)piperazine
1-(2-pyrazinyl)piperazine,
1-benzylpiperazine,
N-ethoxycarbonylpiperazine,
1-(3,4-methylenedioxybenzyl)piperazine,
1-(4-chloro-benzyl)piperazine,
1-(2-phenylethyl)piperazine,
1-(1-phenylethyl)piperazine,
1-benzhydrylpiperazine,
1-(4,4'-difluorobenzhydryl)piperazine,
1-cinnamylpiperazine,
1-allylpiperazine,
1-isopropylpiperazine,
1-cyclopropylpiperazine,
1-cyclobutylpiperazine,
1-cyclopentylpiperazine,
1-cyclohexylpiperazine,
1-cycloheptylpiperazine,
1-(2-cyclohexylethyl)piperazine,
1-(2-dimethylaminoethyl)piperazine,
1-(2-diethylaminoethyl)piperazine,
1-(3-hydroxypropyl)piperazine,
1-(3-chloropropyl)piperazine,
piperazineoacetomorpholide,
piperazinoacetopyrrolidide,
N-methylpiperazinoacetanilide,
ethyl piperazinoacetate,
4-phenylpiperidine,
4-hydroxypiperidine,
piperidin-4-carboxylic acid,
piperidin-3-carboxylic acid,
4-fluorobenzylamine,
2-chlorobenzylamine,
3-chlorobenzylamine,
4-bromobenzylamine,
2-methylbenzylamine,
4-(t-butyl)benzylamine,
2-methoxybenzylamine,
3-methoxybenzylamine,
4-methoxybenzylamine,
3,4-methylenedioxybenzylamine,
3,4-dimethoxybenzylamine,
3,4,5-trimethoxybenzylamine,
4-trifluoromethylbenzylamine,
4-carboxybenzylamine,
3,5-dimethylbenzylamine,
D(+)-1-phenylethylamine,
L(−)-1-phenylethylamine,
2-aminomethylpyridine,
2-aminomethylthiophene,
2-cyclohexylsulphonylaniline,
2-(3,4-dichlorobenzylsulphonyl)aniline,
2-(3,4-dichlorobenzylsulphonyl)-5-acetylaminoaniline,
2-(3,4-dichlorobenzylsulphonyl)-4-acetylaminoaniline,
2-(phenylsulphonyl)-4-acetylaminoaniline,
2-(3,4-dichlorobenzylsulphonyl)-4-methylaniline,
4-(2-hydroxyethoxy)aniline,
4-(cyclohexylmethoxy)aniline,
(5-ethylsulphonyl-1,3,4-thiadiazol-2-yl)amine,
(5,6-dihydro-4H-1,3-oxazin-2-yl)amine,
2-amino-4-trifluoromethylpyrimidine,
2-hydrazino-4-trifluoromethylpyrimidine,
4,5-bistrifluoromethyl-2-hydrazinopyrimidine,
4,6-bistrifluoromethyl-2-hydrazinopyrimidine,
3,4-bistrifluoromethylaniline,
3,5-bistrifluoromethylaniline,
2-(2-methoxycarbonylphenylthio)-5-methylaniline,
4-methoxyaniline,
2,6-dichloro-4-isobutyoxycarbonylaniline,
4-isobutoxycarbonylaniline,
2-amino-5-dimethylamino-1,3,4-thiadiazole,
1-amino-4-hydroxymethylpiperidine,
6-amino-5-chloro-8-methoxy-2-methylquinoline,
4-(5-methylhexyloxy)aniline,
4-(pyridylmethoxy)aniline or
4-ethoxyaniline.

It was surprisingly found in the context of investigations which led to the present invention that the compounds of the general formula (I) according to the invention possess an exceedingly strong action against viruses and, in particular, against both DNA viruses and also RNA viruses. The DNA viruses include, for example, the piconda-, papova-, adeno-, herpes-, hepatitis- and smallpox viruses. The RNA virus group includes, for example, the picorna-, reo-, toga-, corona-, othomyxo- and rhabdo viruses. The compounds according to the invention are particularly effective against the retroviruses included by the RNA viruses. This is illustrated by the experimental data indicated further below, for example, for the compounds on Visna virus in cell cultures. Visna virus and HIV virus (Human Immunodeficiency Virus) both belong to the retrovirus subfamily of the Lentiviruses [Haase A. T., Nature (1986) 322, 130–136]. Both viruses have a similar genome organization and a complex transcription pattern compared to the other retroviruses [Sonijo P. et al., Cell (1985), 42, 369–382; Davis J. L. et al., Journal of Virology (1987) 61 (5) 1325–1331]).

In cell cultures which are infected with Visna virus, pronounced virus-induced, cytopathic effects appear 5 to 10 days after infection. By treatment of the infected cell cultures with the compounds according to the invention, the appearance of these cytopathic effects could be prevented.

The Visna virus test was carried out by the method of O. Narayan et al., Journal of Infectious Diseases 135, 5, 1977, 800–806. For this, the compounds according to the invention were diluted to non-cytotoxic concentrations in culture medium in 96-well microtiter plates.

Subsequently, sheep fibroblast cells ($5 \times 10^4$ cells per well) in production medium were added to each well. Each well then contained 50 μl of a Visna virus solution having a titre of about $2.5 \times 10^4$ TCID$_{50}$ (TCID=tissue culture infectious dose). This virus dose corresponds to an MOI (multiplicity of infection) of about 0.05.

Under these infection conditions, a virus-induced cytopathic effect resulted in one infection control without substance between day 5 and day 10. The infected and treated cells and the controlled cells were incubated for 7 days at 37° C. and 5% $CO_2$.

On appearance of the virus-induced cytopathogenic effect in the untreated virus control, the cultures were fixed using formalin and subsequently stained with a Giemsa solution. The inhibitory concentration (IC$_{50}$) was determined microscopically as the concentration at which the cytopathic effect was inhibited by 50% in comparison to the untreated virus control which exhibited 100% cell destruction.

It was found, for example, that N-(4-ethoxyphenyl)-3-(1,5-didesoxy-1,5-imino-D-glucit-N-yl)propionamide protects the cells infected with Visna virus from virus-induced cell destruction in a concentration range from 500 μg/ml to 15 μg/ml.

Typical actions which were found for the compounds according to the invention are listed in Table 1. Herein, MCC denotes cytotoxicity and MIC denotes the minimum concentration at which an inhibition of virus multiplication was still observed.

TABLE 1

| Examp. No. | 1 MCC μg/ml | 2 MIC μg/ml | Examp. No. | 1 MCC μg/ml | 2 MIC μg/ml |
|---|---|---|---|---|---|
| 4 | >1000 | 125 | 60 | >1000 | 500 |
| 7 | >1000 | 500 | 66 | 1000 | 500 |
| 10 | >1000 | 30 | 68 | 500 | 250 |
| 11 | >1000 | 500 | 72 | >1000 | 500 |
| 12 | 1000 | 250 | 76 | >1000 | 500 |
| 14 | >1000 | 125 | 82 | >1000 | 500 |
| 16 | >1000 | 250 | 87 | >1000 | 250 |
| 17 | 1000 | 125 | 89 | 1000 | 500 |
| 18 | >1000 | 500 | 90 | 1000 | 250 |
| 19 | >1000 | 125 | 92 | >1000 | 250 |
| 23 | 150 | 75 | 93 | >1000 | 500 |
| 24 | >1000 | 125 | 94 | >1000 | 500 |
| 25 | >1000 | 250 | 96 | >1000 | 500 |
| 27 | >1000 | 250 | 99 | >1000 | 125 |
| 28 | >1000 | 500 | 00 | >1000 | 500 |
| 29 | >1000 | 125 | 89 | 1000 | 500 |
| 31 | >1000 | 125 | 90 | 1000 | 250 |
| 32 | >1000 | 250 | 92 | >1000 | 250 |
| 34 | >1000 | 15 | 93 | >1000 | 500 |
| 35 | 250 | 15 | 94 | >1000 | 500 |
| 38 | 1000 | 250 | 96 | >1000 | 500 |
| 40 | >1000 | 15 | 99 | >1000 | 125 |
| 41 | 1000 | 125 | 100 | >1000 | 500 |
| 43 | >1000 | 500 | 101 | 1000 | 125 |
| 50 | 1000 | 250 | 102 | >1000 | 125 |
| 51 | 1000 | 250 | 103 | >1000 | 125 |
| 53 | 500 | 250 | 104 | >1000 | 250 |
| 54 | 1000 | 250 | 107 | >1000 | 500 |
| 55 | 1000 | 250 | | | |

Since they change the glycosylation pattern of the virus proteins, the compounds according to the invention can also be used in the production of attenuated or noninfectious virus particles which in turn can be employed for vaccine production.

The compounds to be used according to the invention therefore represent valuable active compounds in human and veterinary medicine for the treatment and prophylaxis of diseases produced by retroviruses.

Indication areas which may be mentioned in human medicine, for example, are:

(1) The treatment or prophylaxis of human retrovirus infections.

(2) The treatment or prophylaxis of diseases (AIDS) caused by HIV (Human Immunodeficiency Virus; formerly named HTLV III/LAV) and the stages such as ARC (AIDS related complex) and LAS (lymphadenopathy syndrome) associated with it, and also the hypoimmunity and encephalopathy caused by this virus.

(3) The treatment or the prophylaxis of an HTLV I or HTLV II infection.

(4) The treatment or the prophylaxis of the AIDS carrier condition.

Indications in veterinary medicine which may be mentioned, for example, are:

Infections with (a) Maedivisna (in sheep and goats)
(b) progressive Pneumonia virus (PPV) (in sheep and goats)
(c) caprine arthritic encephalitis virus (in sheep and goats)
(d) Zwoegerziekte virus (in sheep)
(e) infectious anaemia virus (of the horse)
(f) infections caused by feline leukaemia virus The present invention includes pharmaceutical preparations which contain one or more compounds of the formula (I) or which consist of one or more active compounds of the formula (I) in addition to non-toxic, inert pharmaceutically suitable excipients, and processes for the production of these preparations.

The present invention also includes pharmaceutical preparations in dosage units. This means that the preparation is present in the form of individual parts, for example tablets, dragees, capsules, pills, suppositories and ampoules, whose active compound content corresponds to a fraction or a multiple of an individual dose. The dosage units may contain, for example, 1, 2, 3 or 4 individual doses or ½, ⅓ or ¼ of an individual dose. An individual dose preferably contains the amount of active compound which is administered in one application and which usually corresponds to a whole, a half, a third or a quarter of a daily dose.

Non-toxic, inert, pharmaceutically suitable excipients are taken to mean solid, semi-solid or liquid diluents, fillers and formulation auxiliaries of any type.

Preferred pharmaceutical preparations which may be mentioned are tablets, dragees, capsules, pills, granules, suppositories, solutions, suspensions and emulsions, pastes, ointments, gels, creams, lotions, powders and sprays.

Tablets, dragees, capsules, pills and granules may contain the active compound(s) in addition to the customary excipients, such as (a) fillers and extenders, for example starches, lactose, sucrose, glucose, mannitol and silica, (b) binders, for example carboxymethylcellulose, alginates, gelatin and polyvinylpyrrolidone, (c) humectants, for example glycerol, (d) disintegrants, for example agar-agar, calcium carbonate and sodium carbonate, (e) solution retardants, for example paraffin, and (f) absorption accelerators, for example quaternary ammonium compounds, (g) wetting agents, for example cetyl alcohol and glycerol monostearate, (h) absorbants, for example kaolin and bentonite and (i) lubricants, for example talc, calcium stearate and magnesium stearate and solid polyethylene glycols or mixtures of the substances mentioned under (a) to (i).

The tablets, dragees, capsules, pills and granules may be mixed with the customary coatings and shells, if appropriate containing opacifying agents, and may also be composed so that they release the active compound(s), if appropriate with a delay, only or preferably in a certain part of the intestinal tract, for which purpose, for example, polymeric substances and waxes can be used as embedding materials.

If appropriate, the active compound(s) may also be present in microencapsulated form with one or more of the abovementioned excipients.

In addition to the active compound(s), suppositories may contain the customary water-soluble or water-insoluble excipients, for example polyethylene glycols, fats, for example cocoa fat and higher esters (for example $C_{14}$-alcohol with $C_{16}$-fatty acid), or mixtures of these substances.

Ointments, pastes, creams and gels may contain the customary excipients in addition to the active compound(s), for example animal and vegetable fats, waxes, paraffins, starch, tragacanth, cellulose derivatives, polyethylene glycols, silicones, bentonites, silica, talc and zinc oxide or mixture of these substances.

Powders and sprays may contain the customary excipients in addition to the active compound(s), for example lactose, talc, silica, aluminum hydroxide, calcium silicate and polyamide powder or mixtures of these substances, and sprays may additionally contain the customary propellants, for example chlorofluorohydrocarbons.

Solutions and emulsions may contain the customary excipients, such as solvents, solution retardants and emulsifiers, for example water, ethyl alcohol, isopropyl alcohol, ethyl carbonate, ethyl acetate, benzyl alcohol, benzyl benzoates, propylene glycol, 1,3-butylene glycol, dimethylformamide, oils, in particular cotton seed oil, groundnut oil, maize germ oil, olive oil, castor oil and sesame oil, glycerol, glycerol formal, tetrahydrofurfuryl alcohol, polyethylene glycols and fatty acid esters of sorbitan or mixtures of these substances in addition to the active compound(s).

For parenteral administration, the solutions and emulsions may also be present in sterile and blood-isotonic form.

Suspensions may contain the customary excipients, such as liquid diluents, for example water, ethyl alcohol, propylene glycol, suspending agents, for example ethoxylated isostearyl alcohols, polyoxyethylene sorbitol and sorbitan esters, microcrystalline cellulose, aluminum metahydroxide, bentonite, agar-agar and tragacanth or mixtures of these substances in addition to the active compound(s).

The formulation forms mentioned may also contain colorants, preservatives and also odor-improving and flavor-improving additives, for example peppermint oil and eucalyptus oil, and sweeteners, for example saccharin.

The active compounds of the formula (I) should preferably be present in the abovementioned pharmaceutical preparations in a concentration of about 0.1 to 99.5, preferably 0.15 to 95% by weight, of the total mixture.

The abovementioned pharmaceutical preparations may also contain further pharmaceutically active compounds in addition to the compounds of the formula (I).

The production of the abovementioned pharmaceutical preparations takes place in a customary manner by known methods, for example by mixing the active compound(s) with the excipient(s).

The preparations mentioned may be used either orally, rectally, parenterally (intravenously, intramuscularly, subcutaneously), intracisternally, intravaginally, intraperitoneally, locally (powders, ointments, drops) in humans and animals and for the therapy of infections in hollow spaces and body cavities. Suitable preparations are injection solutions, solutions and suspensions for oral treatment, gels, formulations for pouring on, emulsions, ointments or drops. For local treatment, ophthalmological and dermatological formulations, silver salts and other salts, ear drops, eye ointments, powders or solutions may be used. In animals, the administration can also take place in suitable formulations via the feed or drinking water. Furthermore, gels, powders, tablets, delayed-release tablets, premixes, concentrates, granules, pellets, boli, capsules, aerosols, sprays and inhalants can be used in humans and animals. Furthermore, the compounds according to the invention can be incorporated in other excipients such as, for example, plastics (plastic chains for local treatment), collagen or bone cement.

In general, it has proved advantageous both in human and veterinary medicine to administer the active compound(s) of the formula (I) in total amounts of about 0.5 to about 500, preferably 5 to 100 mg/kg of body weight every 24 hours, if appropriate in the form of several individual doses, to obtain the desired results. An individual dose preferably contains the active compound(s) in amounts from about 1 to about 80, in particular 3 to 30 mg/kg of body weight. However, it may be necessary to deviate from the dosages mentioned depending on the species and the body weight of the subject to be treated, the nature and severity of the disease, the type of the preparation and the administration of the medicament and also the time period or interval within which the administration takes place.

Thus, in some cases it may be sufficient to manage with less than the abovementioned amount of active compound, whereas in other cases the abovementioned amount of active compound must be exceeded. The optimum dosage required in each case and the type of administration of the active compound can easily be established by one skilled in the art on the basis of his expert knowledge.

The compounds to be used according to the invention can be given in the customary concentrations and preparations together with the feed or with feed preparations or with the drinking water.

PREPARATION EXAMPLES

Example 1

N-(4-Methoxyphenyl)-3-(1,5-didesoxy-1,5-imino-D-glucit-N-yl)propionamide

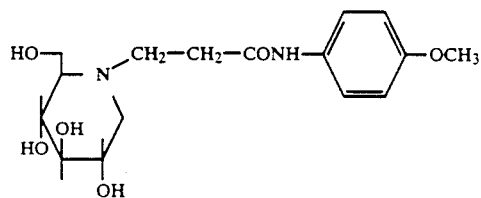

2 g (8.5 mmol) of N-(2-carboxyethyl)-1-desoxynojirimycin are dissolved in a mixture of 11 ml of water and 22 ml of pyridine. The solution is cooled to 0° C. A solution of 1.9 g (9.4 mmol) of dicyclohexylcarbodiimide in pyridine is added and the mixture is left at 0° for 120 minutes. 1.3 g (10.2 mmol) of p-methoxy aniline are then added. The cooling is removed and the reaction mixture is stirred at room temperature. After 8 hours, substantial reaction is detected by thin-layer chromatography (chloroform:methanol:ammonia solution=4:3:1 v/v system).

The solid material is filtered off, the solvent is evaporated in high vacuum and the residue is chromatographed on 200 g of silica gel (mobile phase methylene chloride:ethanol:triethylamine=4:1:0.005). 2.5 g (7.2 mmol, 85%) of product are isolated. $R_f=0.60$ (chloroform:methanol:ammonia=4:3:1)

Example 2
N-(4-Oxymethylenemethoxycarbonylphenyl)-3-(1,5-didesoxy-1,5-imino-D-glucit-N-yl)propionamide

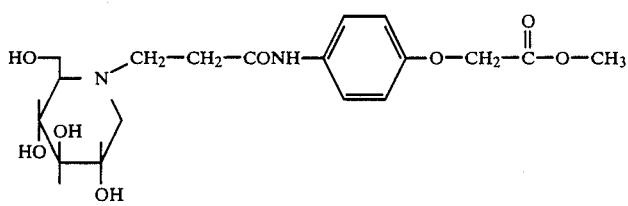

In accordance with the directions for Example 1, 8.5 mmol of N-(2-carboxyethyl)desoxynojirimycin are reacted with 10 mmol of 4-oxymethylenemethoxycarbonylaniline.
Yield: 1.45 g.
Melting point: 103° C., $R_f=0.60$.
$[\alpha]_D^{20}=-36°$ (c=1, methanol).

Example 3
N-[4-(4-Pyridylmethoxyphenyl)]-3-(1,5-didesoxy-1,5-imino-D-glucit-N-yl)propionamide

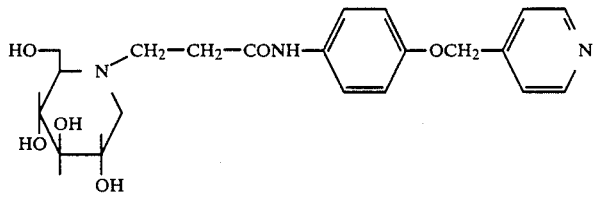

In accordance with the description for Example 1, 8.5 mmol of N-(2-carboxyethyl)desoxynojirimycin are reacted with 10 mmol of 4-(4-pyridylmethoxy)aniline.
Yield: 0.86 g.
Melting point: 172° C., $R_f=0.6$.
$[\alpha]_D^{20}=-38°$ (c=1, methanol).

Example 4
N-(4-Benzyloxyphenyl)-3-(1,5-didesoxy-1,5-imino-D-glucit-N-yl)propionamide

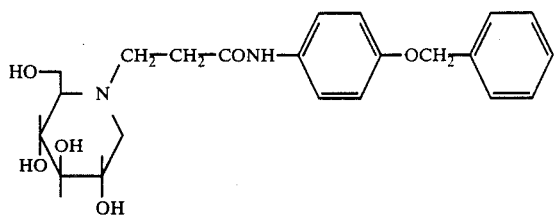

In accordance with the description for Example 1, 8.5 mmol of N-(2-carboxyethyl)desoxynojirimycin are reacted with 10 mmol of 4-benzyloxyaniline.
Yield: 1.26 g.
Melting point: 124° C., $R_f=0.68$.
$[\alpha]_D^{20}=-25°$ (c=1, methanol).

Example 5
N-(4-Trifluoromethoxyphenyl)-3-(1,5-didesoxy-1,5-imino-D-glucit-N-yl)-propionamide

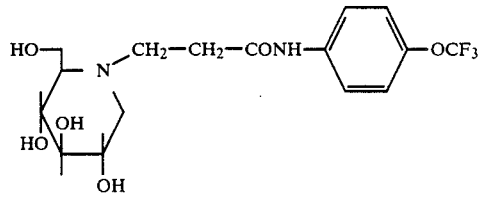

In accordance with the description for Example 1, 8.5 mmol of N-(2-carboxyethyl)desoxynojirimycin are reacted with 10 mmol of 4-trifluoromethoxyaniline.
$R_f=0.64$.

Example 6

N-(4-Hydroxyphenyl)-3-(1,5-didesoxy-1,5-imino-D-glucit-N-yl)propionamide

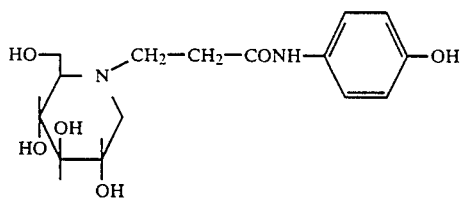

In accordance with the description for Example 1, 8.5 mmol of N-(2-carboxyethyl)desoxynojirimycin are reacted with 10 mmol of 4-hydroxyaniline.
$R_f=0.65$.
$[\alpha]_D^{20}=-25°$ (c=1, methanol).

Example 7

N-(4-Tert.-butylphenyl)-3-(1,5-didesoxy-1,5-imino-D-glucit-N-yl)propionamide

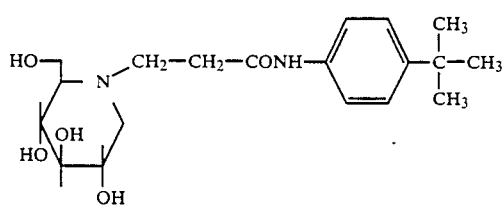

In accordance with the description for Example 1, 8.5 mmol of N-(2-carboxyethyl)desoxynojirimycin are reacted with 10 mmol of 4-tert.-butylaniline.
Yield: 1.97 g.
Melting point: 76° C., $R_f=0.68$.
$[\alpha]_D^{20}=-35°$ (c=1, methanol).

Example 8

N-[4-(6-Methylheptyloxy)phenyl]-3-(1,5-didesoxy-1,5-imino-D-glucit-N-yl)propionamide

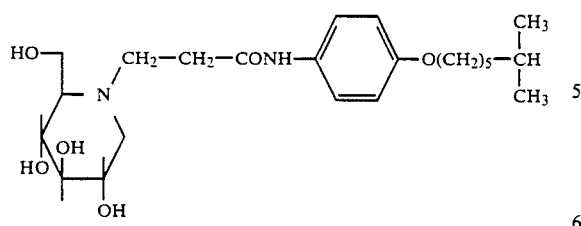

In accordance with the description for Example 1, 8.5 mmol of N-(2-carboxyethyl)desoxynojirimycin are reacted with 10 mmol of 4-(6-methylheptyloxy)aniline.
Yield: 1.39 g.
Melting point: colorless resin, $R_f=0.72$.
$[\alpha]_D^{20}=-29°$ (c=1, methanol).

Example 9

N-[4-(2-N,N-Diethylaminoethoxy)phenyl]-3-(1,5-didesoxy-1,5-imino-D-glucit-N-yl)propionamide

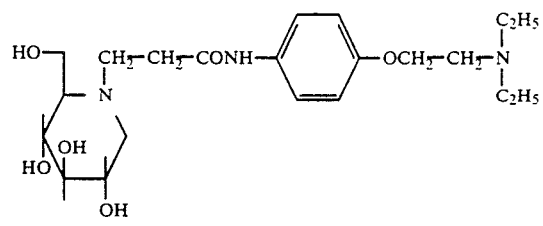

In accordance with the description for Example 1, 8.5 mmol of N-(2-carboxyethyl)desoxynojirimycin are reacted with 10 mmol of 4-(2-N,N-diethylaminoethoxy)aniline.
Yield: 1.44 g.
Melting point: colorless resin, $R_f=0.67$.
$[\alpha]_D^{20}=-28°$ (c=1, methanol).

Example 10

N-(4-Allyloxyphenyl)-3-(1,5-didesoxy-1,5-imino-D-glucit-N-yl)propionamide

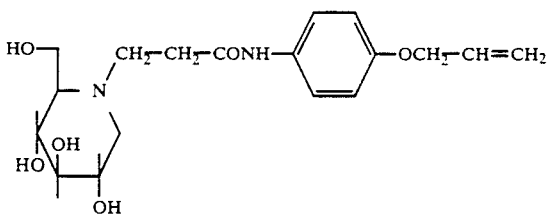

In accordance with the description for Example 1, 8.5 mmol of N-(2-carboxyethyl)desoxynojirimycin are reacted with 10 mmol of 4-allyloxyaniline.
Yield: 1.0 g.
Melting point: 139° C., $R_f=0.66$.
$[\alpha]_D^{20}=-36°$ (c=1, methanol).

Example 11

N-(4-Trifluoromethylphenyl)-3-(1,5-didesoxy-1,5-imino-D-glucit-N-yl)propionamide

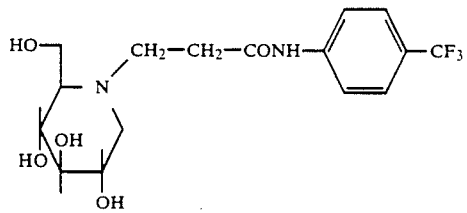

In accordance with the description for Example 1, 8.5 mmol of N-(2-carboxyethyl)desoxynojirimycin are reacted with 10 mmol of 4-trifluoromethylaniline.
Yield: 0.72 g.
Melting point: colorless resin, $R_f=0.65$.
$[\alpha]_D^{20}=-24°$ (c=1, methanol).

Example 12

N-[4-(2-Chloro-1,1,2-trifluoroethoxy)phenyl]-3-(1,5-didesoxy-1,5-imino-D-glucit-N-yl)propionamide

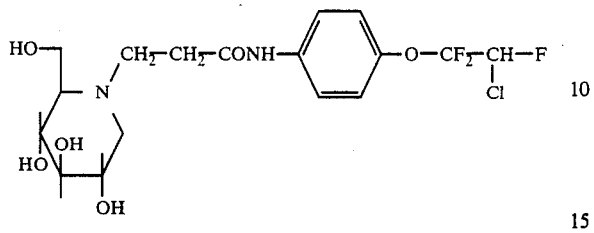

In accordance with the description for Example 1, 8.5 mmol of N-(2-carboxyethyl)desoxynojirimycin are reacted with 10 mmol of 4-(2-chloro-1,1,2-trifluoroethoxy)aniline.
Yield: 1.36 g.
Melting point: colorless resin, $R_f=0.64$.
$[\alpha]_D^{20}=27°$ (c=1, methanol).

Example 13

N-(4-Isopropylphenyl)-3-(1,5-didesoxy-1,5-imino-D-glucit-N-yl)propionamide

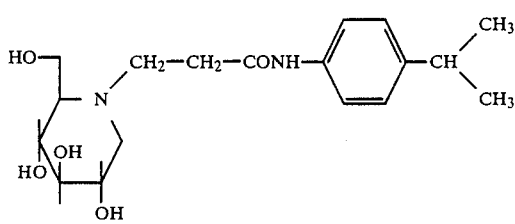

In accordance with the description for Example 1, 8.5 mmol of N-(2-carboxyethyl)desoxynojirimycin are reacted with 10 mmol of 4-isopropylaniline.
Yield: 1.7 g.
Melting point: colorless resin, $R_f=0.64$.
$[\alpha]_D^{20}=-38°$ (c=1, methanol).

Example 14

N-(2-Isopropylphenyl)-3-(1,5-didesoxy-1,5-imino-D-glucit-N-yl)propionamide

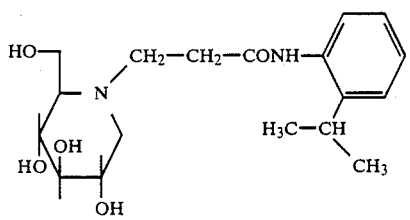

In accordance with the description for Example 1, 8.5 mmol of N-(2-carboxyethyl)desoxynojirimycin are reacted with 10 mmol of 2-isopropylaniline.
Yield: 1.05 g.
Melting point: 156° C., $R_f=0.68$.
$[\alpha]_D^{20}=-32°$ (c=1, methanol).

Example 15

N-(4-Fluorophenyl)-3-(1,5-didesoxy-1,5-imino-D-glucit-N-yl)propionamide

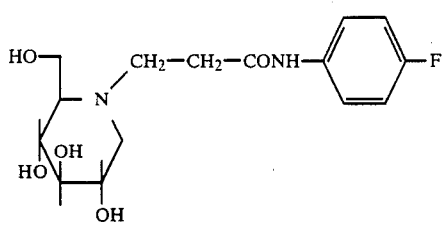

In accordance with the description for Example 1, 8.5 mmol of N-(2-carboxyethyl)desoxynojirimycin are reacted with 10 mmol of 4-fluoroaniline.
Yield: 1.7 g.
Melting point: colorless resin, $R_f=0.58$.
$[\alpha]_D^{20}=-31°$ (c=1, methanol).

Example 16

N-(2-Fluorophenyl)-3-(1,5-didesoxy-1,5-imino-D-glucit-N-yl)propionamide

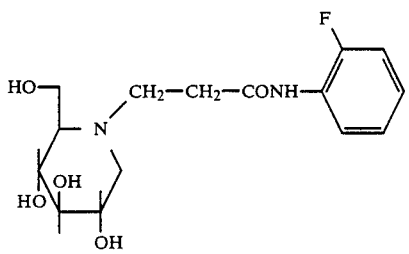

In accordance with the description for Example 1, 8.5 mmol of N-(2-carboxyethyl)desoxynojirimycin are reacted with 10 mmol of 4-fluoroaniline.
Yield: 0.92 g.
Melting point: 169° C., $R_f=0.66$.
$[\alpha]_D^{20}=-23°$ (c=1, methanol).

Example 17

1-[3-(1,5-Didesoxy-1,5-imino-D-glucit-N-yl)propionyl]-2,3-dihydroindole

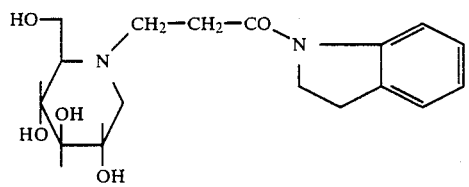

In accordance with the description for Example 1, 8.5 mmol of N-(2-carboxyethyl)desoxynojirimycin are reacted with 10 mmol of 2,3-dihydroindole.
Yield: 1.2 g.
Melting point: 198°, $R_f=0.7$.
$[\alpha]_D^{20}=-42°$ (c=1, methanol).

Example 18

N-(2,4-Difluorophenyl)-3-(1,5-didesoxy-1,5-imino-D-glucit-N-yl)propionamide

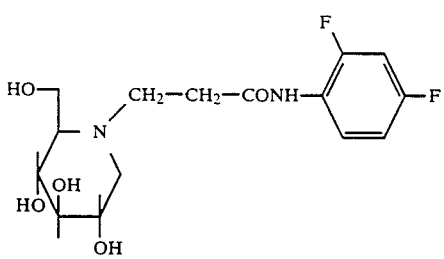

In accordance with the description for Example 1, 8.5 mmol of N-(2-carboxyethyl)desoxynojirimycin are reacted with 10 mmol of 2,4-difluoroaniline.
Yield: 1.03 g.
Melting point: 166° C., $R_f=0.65$.
$[\alpha]_D^{20} = -24°$ (c=1, methanol).

Example 19

N-(3,4-Difluorophenyl)-3-(1,5-didesoxy-1,5-imino-D-glucit-N-yl)propionamide

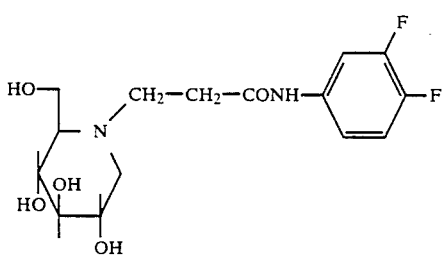

In accordance with the description for Example 1, 8.5 mmol of N-(2-carboxyethyl)desoxynojirimycin are reacted with 10 mmol of 3,4-difluoroaniline.
Yield: 1.33 g.
Melting point: colorless resin, $R_f=0.64$.
$[\alpha]_D^{20} = -26°$ (c=1, methanol).

Example 20

N-(2-Trifluoromethylphenyl)-3-(1,5-didesoxy-1,5-imino-D-glucit-N-yl)propionamide

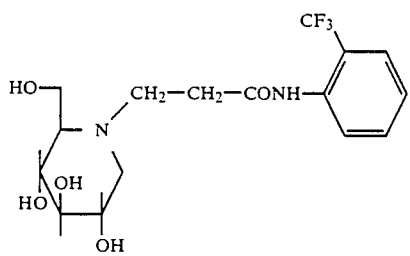

In accordance with the description for Example 1, 8.5 mmol of N-(2-carboxyethyl)desoxynojirimycin are needed with 10 mmol of 2-trifluoromethylaniline.
Yield:.
$R_f=0.62$.

Example 21

N-(2,6-Difluorophenyl)-3-(1,5-didesoxy-1,5-imino-D-glucit-N-yl)propionamide

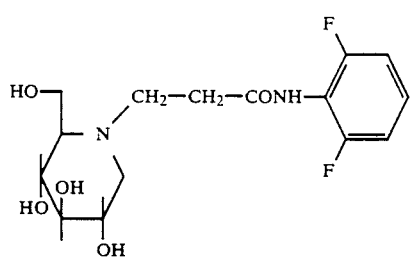

In accordance with the description for Example 1, 8.5 mmol of N-(2-carboxyethyl)desoxynojirimycin are reacted with 10 mmol of 2,6-difluoroaniline.
$R_f=0.62$.

Example 22

N-(Adamantan-1-yl)-3-(1,5-didesoxy-1,5-imino-D-glucit-N-yl)propionamide

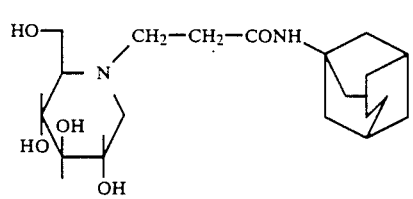

In accordance with the description of Example 1, 8.5 mmol of N-(2-carboxyethyl)desoxynojirimycin are reacted with 10 mmol of 1-aminoadamantane.
$R_f=0.62$.

Example 23

N-(3,4,5-Trimethoxyphenyl)-3-(1,5-didesoxy-1,5-imino-D-glucit-N-yl)propionamide

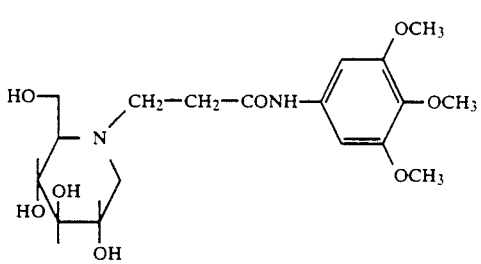

In accordance with the description for Example 1, 8.5 mmol of N-(2-carboxyethy)desoxynojirimycin are reacted with 10 mmol of 3,4,5-trimethoxyaniline.
Yield: 2.16 g.
Melting point: colorless resin, $R_f=0.68$.
$[\alpha]_D^{20} = -29°$ (c=1, methanol).

Example 24

N-(3,4-Dimethoxyphenyl)-3-(1,5-didesoxy-1,5-imino-D-glucit-N-yl)propionamide

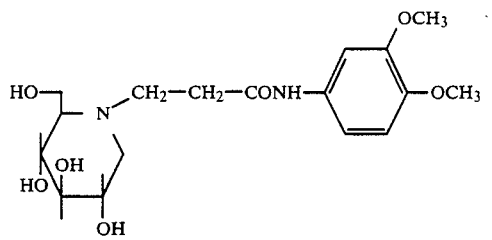

In accordance with the description for Example 1, 8.5 mmol of N-(2-carboxyethyl)desoxynojirimycin are reacted with 10 mmol of 3,4-dimethoxyaniline.
Yield: 1.78 g.
Melting point: 157° C., $R_f$=0.65.
$[\alpha]_D^{20}$= −43° (c=1, methanol).

Example 25

N-(3,5-Dimethoxyphenyl)-3-(1,5-didesoxy-1,5-imino-D-glucit-N-yl)propionamide

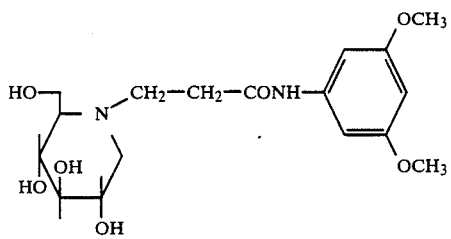

In accordance with the description for Example 1, 8.5 mmol of N-(2-carboxyethyl)desoxynojirimycin are reacted with 10 mmol of 3,5-dimethoxyaniline.
Yield: 1.82 g.
Melting point: 106° C., $R_f$=0.68.
$[\alpha]_D^{20}$= −35° (c=1, methanol).

Example 26

N-(2,4,6-Tribromophenyl)-3-(1,5-didesoxy-1,5-imino-D-glucit-N-yl)propionamide

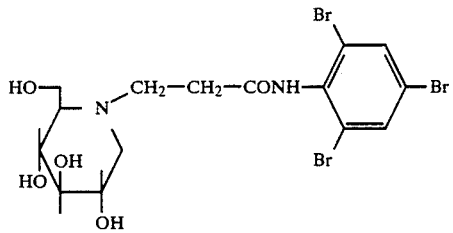

In accordance with the description for Example 1, 8.5 mmol of N-(2-carboxyethyl)desoxynojirimycin are reacted with 10 mmol of 2,4,6-tribromoaniline.
Yield: 0.98 g.
Melting point: 194° C., $R_f$=0.62.
$[\alpha]_D^{20}$= −16° (c=1, methanol).

Example 27

N-(3-Cyanophenyl)-3-(1,5-didesoxy-1,5-imino-D-glucit-N-yl)propionamide

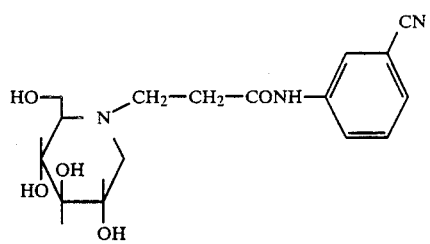

In accordance with the description for Example 1, 8.5 mmol of N-(2-carboxyethyl)desoxynojirimycin are reacted with 10 mmol of 3-cyanoaniline.
Yield: 0.86.
Melting point: 177° C., $R_f$=0.64.
$[\alpha]_D^{20}$= −22° (c=1, methanol).

Example 28

N-(4-Cyclohexylphenyl)-3-(1,5-didesoxy-1,5-imino-D-glucit-N-yl)propionamide

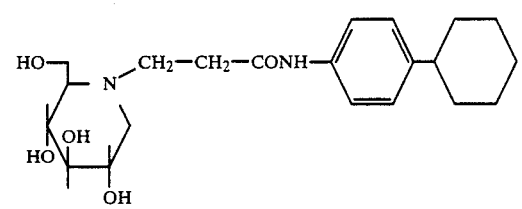

In accordance with the description for Example 1, 8.5 mmol of N-(2-carboxyethyl)desoxynojirimycin are reacted with 10 mmol of 4-cyclohexylaniline.
Yield: 1.9 g.
Melting point: 206° C., $R_f$=0.71.
$[\alpha]_D^{20}$= −34° (c=1, methanol).

Example 29

N-(3,4-Ethylenedioxyphenyl)-3-(1,5-didesoxy-1,5-imino-D-glucit-N-yl)propionamide

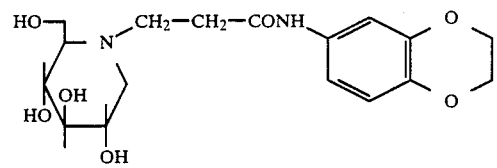

In accordance with the description of Example 1, 8.5 mmol of N-(2-carboxyethyl)desoxynojirimycin are reacted with 10 mmol of 3,4-ethylenedioxyaniline.
Yield: 2.98 g.
Melting point: colorless resin, $R_f$=0.62.
$[\alpha]_D^{20}$= −35° (c=1, methanol).

Example 30

N-(2-Bromophenyl)-3-(1,5-didesoxy-1,5-imino-D-glucit-N-yl)propionamide

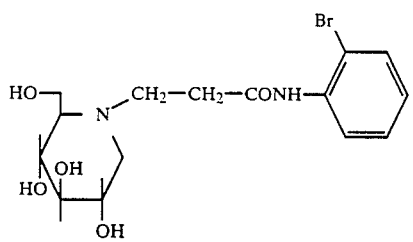

In accordance with the description for Example 1, 8.5 mmol of N-(2-carboxyethyl)desoxynojirimycin are reacted with 10 mmol of 2-bromoaniline.
Yield: 0.89 g.
Melting point: 201° C., $R_f=0.6$.
M+1=390.

EXAMPLE 31

N-(3,4-Methylenedioxyphenyl)-3-(1,5-didesoxy-1,5-imino-D-glucit-N-yl)propionamide

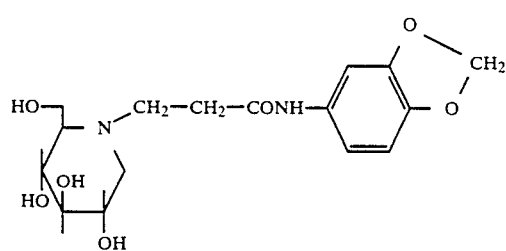

In accordance with the description for Example 1, 8.5 mmol of N-(2-carboxyethyl)desoxynojirimycin are reacted with 10 mmol of 3,4-methylenedioxyaniline.
Yield: 1.59 g.
Melting point: colorless resin, $R_f=0.62$.
$[\alpha]_D^{20}=-37°$ (c=1, methanol).

Example 32

N-(2-Methylthiophenyl)-3-(1,5-didesoxy-1,5-imino-D-glucit-N-yl)propionamide

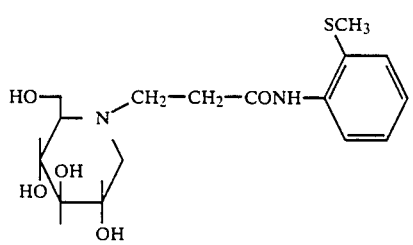

In accordance with the description for Example 1, 8.5 mmol of N-(2-carboxyethyl)desoxynojirimycin are reacted with 10 mmol of 2-methylthioaniline.
Yield: 0.8 g.
Melting point: 201° C., $R_f=0.68$.

Example 33

3-(1,5-Didesoxy-1,5-imino-D-glucit-N-yl)-propionyl-4-(4-trifluoromethylphenyl)piperazine

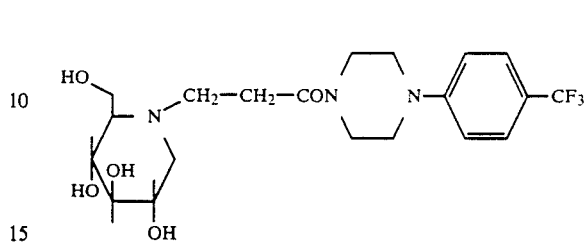

In accordance with the description for Example 1, 8.5 mmol of N-(2-carboxyethyl)desoxynojirimycin are reacted with 10 mmol of 1-(4-trifluoromethylphenyl)piperazine.
Yield: 2.83 g.
Melting point: 179° C., $R_f=0.67$.
$[\alpha]_D^{20}=-11°$ (c=1, methanol).

Example 34

N-Phenyl-3-(1,5-didesoxy-1,5-imino-D-glucit-N-yl)propionamide

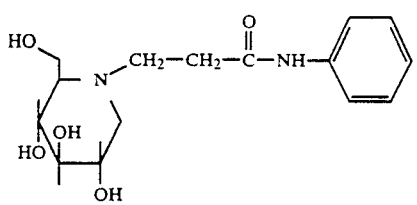

In accordance with the description for Example 1, 8.5 mmol of N-(2-carboxyethyl)desoxynojirimycin are reacted with 10 mmol of aniline.
Melting point: 145° C., $R_f=0.52$.

Example 35

N-(4-Ethoxyphenyl)-3-(1,5-didesoxy-1,5-imino-D-glucit-N-yl)propionamide

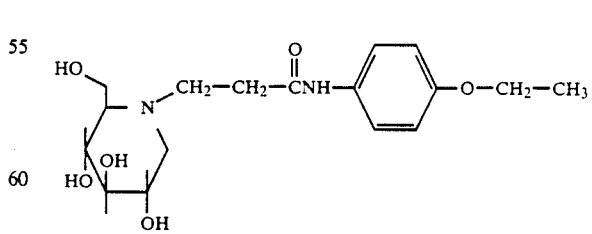

In accordance with the description for Example 1, 8.5 mmol of N-(2-carboxyethyl)desoxynojirimycin are reacted with 10 mmol of 4-ethoxyaniline.
Melting point: 195° C., $R_f=0.52$.

Example 36

N-(2-Dimethylaminoethyl)-3-(1,5-didesoxy-1,5-imino-D-glucit-N-yl)propionamide

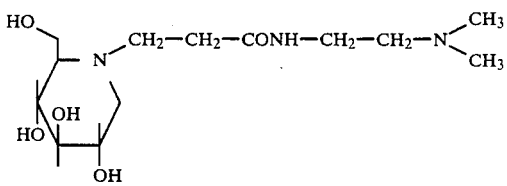

In accordance with the description for Example 1, 8.5 mmol of N-(2-carboxyethyl)desoxynojirimycin are reacted with 10 mmol of 2-dimethylaminoethylamine.
Melting point: 0.9 g.
Melting point: colorless resin, $R_f = 0.59$.
$[\alpha]_D^{20} = -2°$ (c=1, methanol).

Example 37

N-[2-(3-Methoxyphenyl)ethyl]-3-(1,5-didesoxy-1,5-imino-D-glucit-N-yl)propionamide

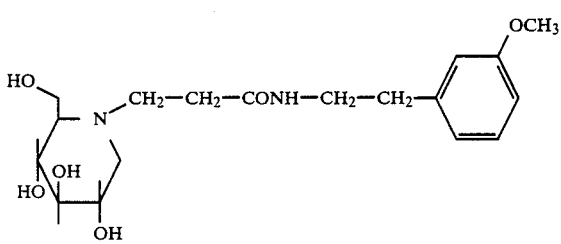

In accordance with the description for Example 1, 8.5 mmol of N-(2-carboxyethyl)desoxynojirimycin are reacted with 10 mmol of 2-(3-methoxyphenyl)ethylamine.
Yield:
$R_f = 0.61$.

Example 38

N-(2-Pyridylmethyl)-3-(1,5-didesoxy-1,5-imino-D-glucit-N-yl)propionamide

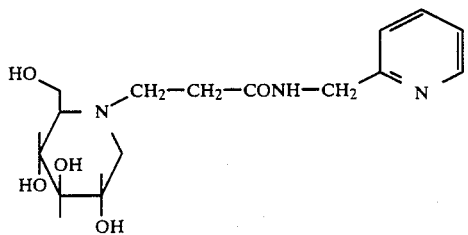

In accordance with the description for Example 1, 8.5 mmol of N-(2-carboxyethyl)desoxynojirimycin are reacted with 10 mmol of 2-aminomethylpyridine.
Yield: 0.75 g.
Melting point: colorless resin, $R_f = 0.51$.
$[\alpha]_D^{20} = -15°$ (c=1, methanol).

Example 39

3-(1,5-Didesoxy-1,5-imino-D-glucit-N-yl)-propionyl-(4-cinnamyl)piperazine

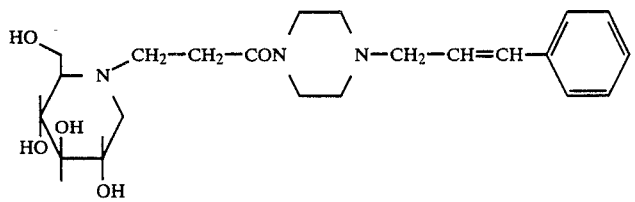

In accordance with the description for Example 1, 8.5 mmol of N-(2-carboxyethyl)desoxynojirimycin are reacted with 10 mmol of 1-cinnamylpiperazine.
$R_f = 0.67$.

Example 40

N-[4-(2-Hydroxyethoxy)phenyl]-3-(1,5-didesoxy-1,5-imino-D-glucit-N-yl)propionamide

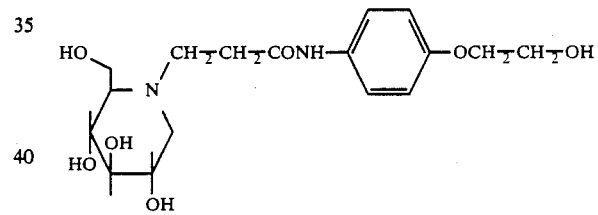

In accordance with the description for Example 1, 8.5 mmol of N-(2-carboxyethyl)desoxynojirimycin are reacted with 10 mmol of 4-(2-hydroxyethoxy)aniline.
Yield:
Melting point: 149° C., $R_f = 0.43$.

Example 41

3-(1,5-Didesoxy-1,5-imino-D-glucit-N-yl)propionyl-1-(4-p-fluorophenyl)piperazine

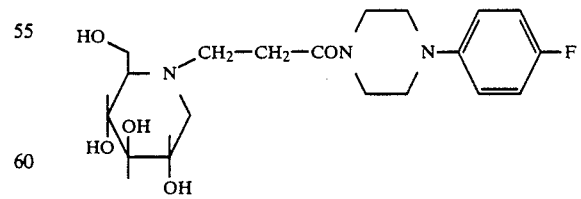

In accordance with the description for Example 1, 8.5 mmol of N-(2-carboxyethyl)desoxynojirimycin are reacted with 10 mmol of 4-fluorophenyl)piperazine.
Yield: 1.2 g.
Melting point: 155° C., $R_f = 0.64$. $[\alpha]_D^{20} = -12°$ (c=1, methanol).

Example 42

N-(4-Methoxyphenyl)-3-(1,5-didesoxy-1,5-imino-D-mannit-N-yl)propionamide

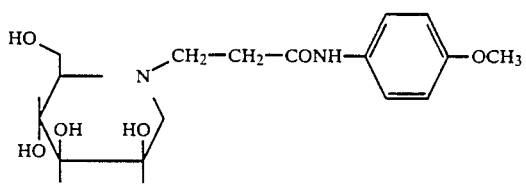

2 g (8.5 mmol) of N-(2-carboxyethyl)-1-desoxymannonojirimycin are dissolved in a mixture of 11 ml of water and 22 ml of pyridine. The solution is cooled to 0°. A solution of 1.9 g (9.4 mmol) of dicyclohexylcarbodiimide in pyridine is added and the mixture is left at 0° C. for 120 minutes. 1.3 g (10.2 mmol) of p-methoxyaniline are then added. The cooling is removed and the reaction mixture is stirred at room temperature. After 8 hours, substantial reaction is detected by thin-layer chromatography (chloroform:methanol:ammonia solution 4:3:1 v/v system).

The solid material is filtered off, the solvent is evaporated in high vacuum and the residue is chromatographed on 200 g of silica gel (mobile phase methylene chloride:ethanol:triethylamine=4:1:0.005). 1.9 g of product are isolated.

$R_f$=0.60 (chloroform:methanol:ammonia=4:3:1).

Example 43

N-(4-Methoxycarbonylphenyl)-3-(1,5-didesoxy-1,5-imino-D-mannit-N-yl)propionamide

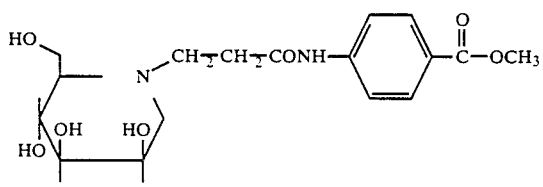

In accordance with the description for Example 1, 8.5 mmol of N-(2-carboxyethyl)-1-desoxymannonojirimycin are reacted with 10 mmol of 4-methoxycarbonylaniline.

$R_f$=0.60.

$[\alpha]_D^{20}$= −27° (c=1, methanol).

Example 44

N-[4-(4-Pyridylmethoxy)phenyl]-3-(1,5-didesoxy-1,5-imino-D-mannit-N-yl)propionamide

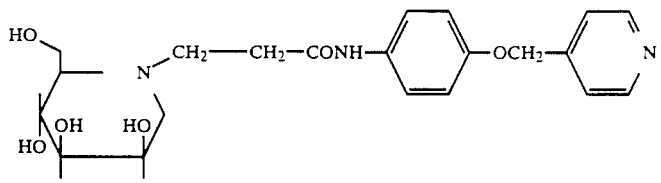

In accordance with the description for Example 1, 8.5 mmol of N-(2-carboxyethyl)-1-desoxymannonojirimycin are reacted with 10 mmol of 4-(4-pyridylmethoxy)aniline.

$R_f$=0.6.

Example 45

N-(4-Benzyloxyphenyl)-3-(1,5-didesoxy-1,5-imino-D-mannit-N-yl)propionamide

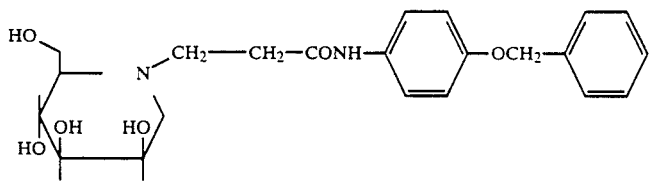

In accordance with the description for Example 1, 8.5 mmol of N-(2-carboxyethyl)-1-desoxymannonojirimycin are reacted with 10 mmol of 4-benzyloxyaniline.

$R_f$=0.68.

$[\alpha]_D^{20}$= −42° (c=1, methanol).

Example 46

N-(4-Trifluoromethylphenyl)-3-(1,5-didesoxy-1,5-imino-D-mannit-N-yl)propionamide

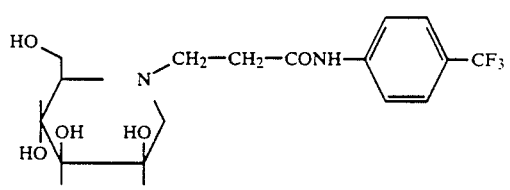

$[\alpha]_D^{20}$= −38° (c=1, methanol).

In accordance with the description for Example 1, 8.5 mmol of N-(2-carboxyethyl)-1-desoxymannonojirimycin are reacted with 10 mmol of 4-trifluoromethoxyaniline.

$R_f$=0.64.

Example 47

N-(4-Hydroxyphenyl)-3-(1,5-didesoxy-1,5-imino-D-mannit-N-yl)propionamide

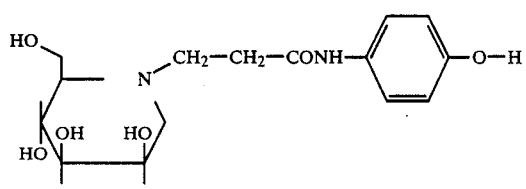

In accordance with the description for Example 1, 8.5 mmol of N-(2-carboxyethyl)-1-desoxymannonojirimycin are reacted with 10 mmol of 4-hydroxyaniline.
$R_f = 0.65$.

Example 48

N-(4-Tert.-butylphenyl)-3-(1,5-didesoxy-1,5-imino-D-mannit-N-yl)propionamide

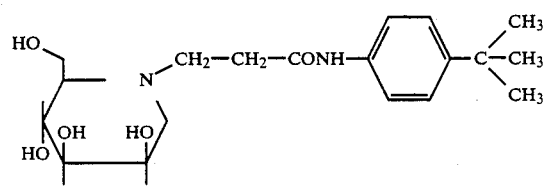

In accordance with the description for Example 1, 8.5 mmol of N-(2-carboxyethyl)-1-desoxymannonojirimycin are reacted with 10 mmol of 4-tert.-butylaniline.
$R_f = 0.68$.
$[\alpha]_D^{20} = -39°$ (c = 1.0, methanol).

Example 49

N-[4-(6-Methylheptyloxy)phenyl]-3-(1,5-didesoxy-1,5-imino-D-mannit-N-yl)propionamide

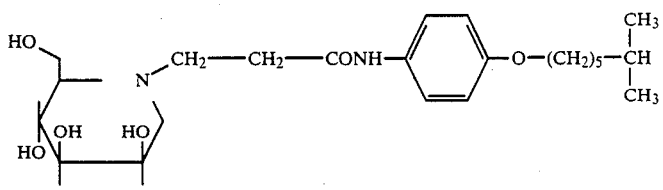

In accordance with the description for Example 1, 8.5 mmol of N-(2-carboxyethyl)-1-desoxymannonojirimycin are reacted with 10 mmol of 4-(6-methylheptyloxy)aniline.
$R_f = 0.72$.
$[\alpha]_D^{20} = -33°$ (c = 1.0, methanol).

Example 50

N-[4-(2-N,N-Diethylaminoethoxy)phenyl]-3-(1,5-didesoxy-1,5-imino-D-mannit-N-yl)propionamide

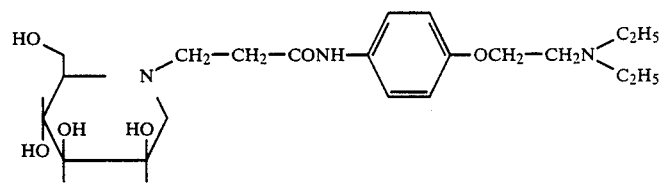

In accordance with the description for Example 1, 8.5 mmol of N-(2-carboxyethyl)-1-desoxymannonojirimycin are reacted with 10 mmol of 4-(2-N,N-diethylaminoethoxy)aniline.
$R_f = 0.67$.
$[\alpha]_D^{20} = -32°$ (c = 1.0, methanol).

Example 51

N-(4-Allyloxyphenyl)-3-(1,5-didesoxy-1,5-imino-D-mannit-N-yl)propionamide

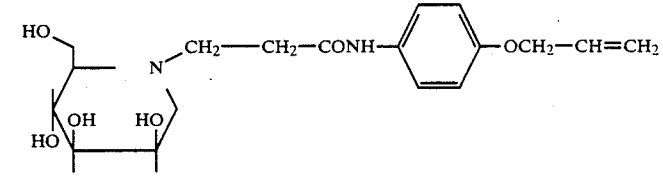

In accordance with the description for Example 1, 8.5 mmol of N-(2-carboxyethyl)-1-desoxymannonojirimycin are reacted with 10 mmol of 4-allyloxyaniline.
$R_f = 0.66$.
$[\alpha]_D^{20} = -45°$ (c = 1.0, methanol).

Example 52

N-(4-Trifluoromethylphenyl)-3-(1,5-didesoxy-1,5-imino-D-mannit-N-yl)propionamide

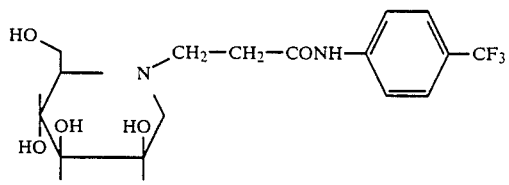

In accordance with the description for Example 1, 8.5 mmol of N-(2-carboxyethyl)-1-desoxymannonojirimycin are reacted with 10 mmol of 4-trifluoromethylaniline.
$R_f$=0.65.
$[\alpha]_D^{20}$= −38° (c=1.0, methanol).

Example 53

N-[4-(2-Chloro-1,1,2-trifluoroethoxy)phenyl]-3-(1,5-didesoxy-1,5-imino-D-mannit-N-yl)propionamide

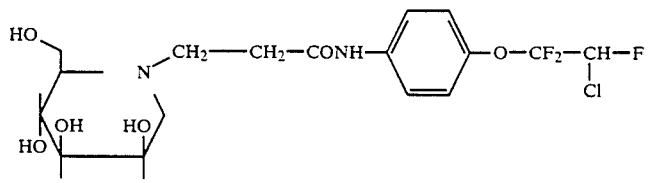

In accordance with the description for Example 1, 8.5 mmol of N-(2-carboxyethyl)-1-desoxymannonojirimycin are reacted with 10 mmol of 4-(2-chloro-1,1,2-trifluoroethoxy)aniline.
$R_f$=0.64.
$[\alpha]_D^{20}$= −38° (c=1.0, methanol).

Example 54

N-(4-Isopropylphenyl)-3-(1,5-didesoxy-1,5-imino-D-mannit-N-yl)propionamide

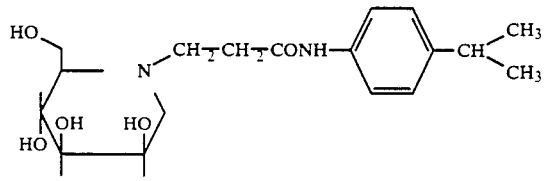

In accordance with the description for Example 1, 8.5 mmol of N-(2-carboxyethyl)-1-desoxymannonojirimycin are reacted with 10 mmol of 4-isopropylaniline.
$R_f$=0.64.
$[\alpha]_D^{20}$= −41° (c=1.0, methanol).

Example 55

N-(2-Isopropylphenyl)-3-(1,5-didesoxy-1,5-imino-D-mannit-N-yl)propionamide

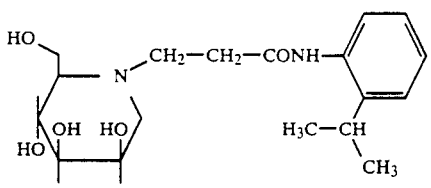

In accordance with the description for Example 1, 8.5 mmol of N-(2-carboxyethyl)-1-desoxymannonojirimycin are reacted with 10 mmol of 2-isopropylaniline.
$R_f$=0.68.
$[\alpha]_D^{20}$= −36° (c=1.0, methanol).

Example 56

N-(4-Fluorophenyl)-3-(1,5-didesoxy-1,5-imino-D-mannit-N-yl)propionamide

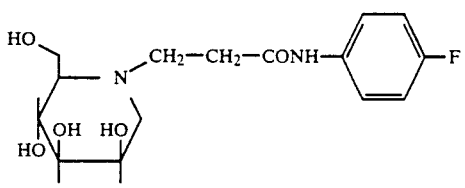

In accordance with the description for Example 1, 8.5 mmol of N-(2-carboxyethyl)-1-desoxymannonojirimycin are reacted with 10 mmol of 4-fluoroaniline.
$R_f$=0.58.
$[\alpha]_D^{20}$= −42° (c=1.0, methanol).

Example 57

N-(2-Fluorophenyl)-3-(1,5-didesoxy-1,5-imino-D-mannit-N-yl)propionamide

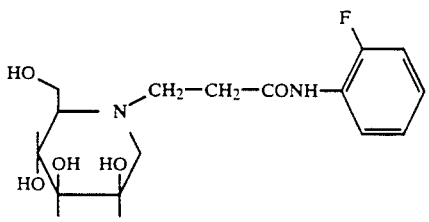

In accordance with the description for Example 1, 8.5 mmol of N-(2-carboxyethyl)-1-desoxymannonojirimycin are reacted with 10 mmol of 2-fluoroaniline.
$R_f$=0.66.
M+1=329.

Example 58

1-[3-(1,5-Didesoxy-1,5-imino-D-mannit-N-yl)-propionyl]-2,3-dihydroindole

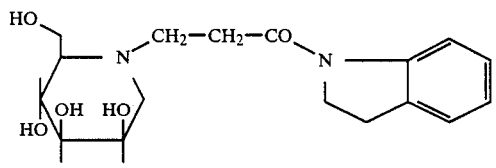

$R_f = 0.64$.
$[\alpha]_D^{20} = -43°$ (c=1, methanol).

In accordance with the description for Example 1, 8.5 mmol of N-(2-carboxyethyl)-1-desoxymannonojirimycin are reacted with 10 mmol of 2,3-dihydroindole.
$R_f = 0.7$.

Example 59

N-(2,4-Difluorophenyl)-3-(1,5-didesoxy-1,5-imino-D-mannit-N-yl)propionamide

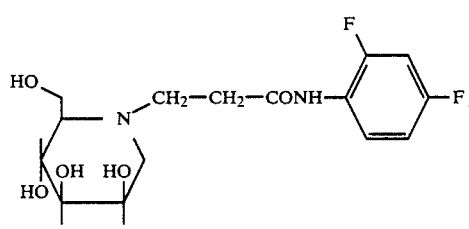

In accordance with the description for Example 1, 8.5 mmol of N-(2-carboxyethyl)-1-desoxymannonojirimycin are reacted with 10 mmol of 2,4-difluoroaniline.
$R_f = 0.65$.
$[\alpha]_D^{20} = -35°$ (c=1.0, methanol).

Example 60

N-(3,4-Difluorophenyl)-3-(1,5-didesoxy-1,5-imino-D-mannit-n-yl)propionamide

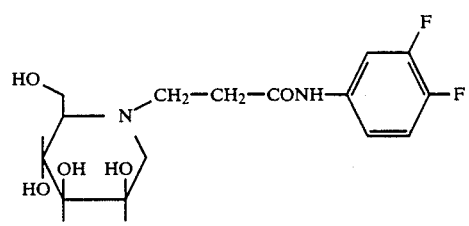

In accordance with the description for Example 1, 8.5 mmol of N-(2-carboxyethyl)-1-desoxymannonojirimycin are reacted with 10 mmol of 3,4-difluoroaniline.
$R_f = 0.64$.
$[\alpha]_D^{20} = -39°$ (c=1.0, methanol).

Example 61

N-(2-Trifluoromethylphenyl)-3-(1,5-didesoxy-1,5-imino-D-mannit-N-yl)propionamide

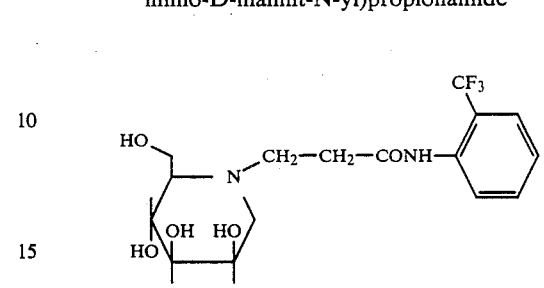

In accordance with the description for Example 1, 8.5 mmol of N-(2-carboxyethyl)-1-desoxymannonojirimycin are reacted with 10 mmol of 2-trifluoromethylaniline.
$R_f = 0.62$.

Example 62

N-(2,6-Difluorophenyl)-3-(1,5-didesoxy-1,5-imino-D-mannit-N-yl)propionamide

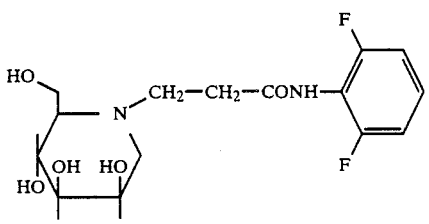

In accordance with the description for Example 1, 8.5 mmol of N-(2-carboxyethyl)-1-desoxymannonojirimycin are reacted with 10 mmol of 2,6-difluoroaniline.
$R_f = 0.62$.

Example 63

N-(Adamantan-1-yl)-3-(1,5-didesoxy-1,5-imino-D-mannit-N-yl)propionamide

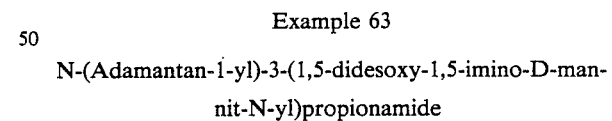

In accordance with the description for Example 1, 8.5 mmol of N-(2-carboxyethyl)-1-desoxymannonojirimycin are reacted with 10 mmol of 1-aminoadamantane.
$R_f = 0.62$.

Example 64

N-(3,4,5-Trimethoxyphenyl)-3-(1,5-didesoxy-1,5-imino-D-mannit-N-yl)propionamide

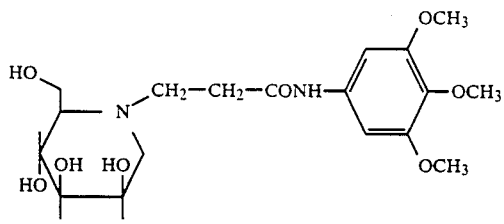

In accordance with the description for Example 1, 8.5 mmol of N-(2-carboxyethyl)-1-desoxymannonojirimycin are reacted with 10 mmol of 3,4,5-trimethoxyaniline. $R_f=0.68$.

$[\alpha]_D^{20}= -32°$ (c=1.0, methanol).

Example 65

N-(3,4-Dimethoxyphenyl)-3-(1,5-didesoxy-1,5-imino-D-mannit-N-yl)-propionamide

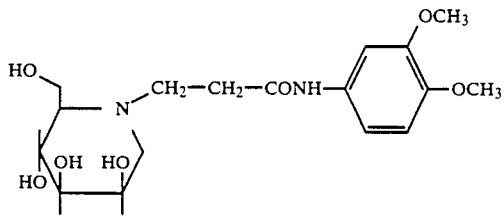

In accordance with the description for Example 1, 8.5 mmol of N-(2-carboxyethyl)-1-desoxymannonojirimycin are reacted with 10 mmol of 3,4-dimethoxyaniline. $R_f=0.65$.

$[\alpha]_D^{20}= -48°$ (c=1.0, methanol).

Example 66

N-(3,5-Dimethoxyphenyl)-3-(1,5-didesoxy-1,5-imino-D-mannit-N-yl)propionamide

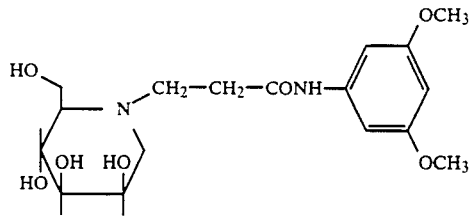

In accordance with the description for Example 1, 8.5 mmol of N-(2-carboxyethyl)-1-mannonojirimycin are reacted with 10 mmol of 3,5-dimethoxyaniline. $R_f=0.68$.

$[\alpha]_D^{20}= -41°$ (c=1.0, methanol).

Example 67

N-(2,4,6-Tribromophenyl)-3-(1,5-didesoxy-1,5-imino-D-mannit-N-yl)propionamide

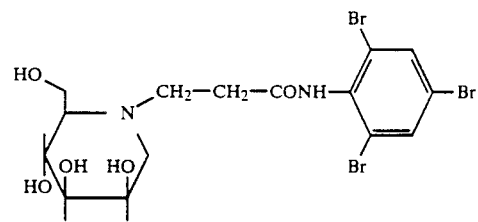

In accordance with the description for Example 1, 8.5 mmol of N-(2-carboxyethyl)-1-desoxymannonojirimycin are reacted with 10 mmol of 2,4,6-tribromoaniline. $R_f=0.62$.

Example 68

N-(3-Cyanophenyl)-3-(1,5-didesoxy-1,5-imino-D-mannit-N-yl)propionamide

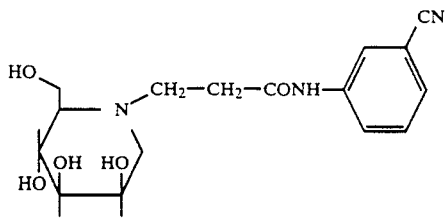

In accordance with the description for Example 1, 8.5 mmol of N-(2-carboxyethyl)-1-desoxymannonojirimycin are reacted with 10 mmol of 3-cyanoaniline. $R_f=0.64$.

$[\alpha]_D^{20}= -49°$ (c=1.0, methanol).

Example 69

N-(4-Cyclohexylphenyl)-3-(1,5-didesoxy-1,5-imino-D-mannit-N-yl)propionamide

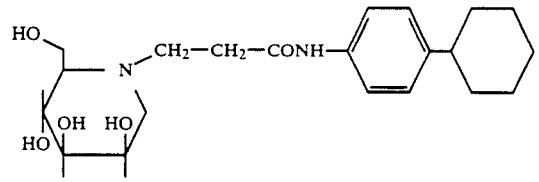

In accordance with the description for Example 1, 8.5 mmol of N-(2-carboxyethyl)-1-desoxymannonojirimycin are reacted with 10 mmol of cyclohexylaniline. $R_f=0.71$.

$[\alpha]_D^{20}= -38$ (c=1.0, methanol).

Example 70

N-(3,4-Ethylenedioxyphenyl)-3-(1,5-didesoxy-1,5-imino-D-mannit-N-yl)propionamide

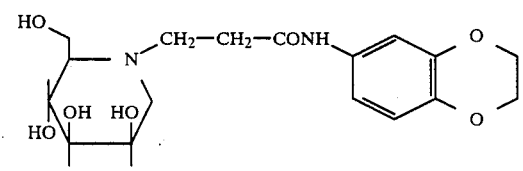

In accordance with the description for Example 1, 8.5 mmol of N-(2-carboxyethyl)-1-desoxymannonojirimycin are reacted with 10 mmol of 3,4-ethylenedioxyaniline.

$R_f = 0.62$.

$[\alpha]_D^{20} = -43°$ (c=1.0, methanol.

EXAMPLE 71

N-(2-Bromophenyl)-3-(1,5-didesoxy-1,5-imino-D-mannit-N-yl)propionamide

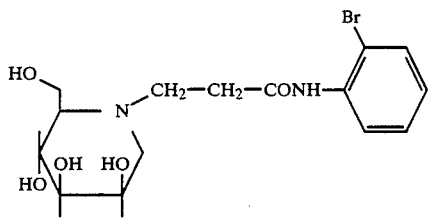

In accordance with the description for Example 1, 8.5 mmol of N-(2-carboxyethyl)-1-desoxymannonojirimycin are reacted with 10 mmol of 2-bromoaniline.

$R_f = 0.6$.

Example 72

N-(3,4-Methylenedioxyphenyl)-3-(1,5-didesoxy-1,5-imino-N-yl)propionamide

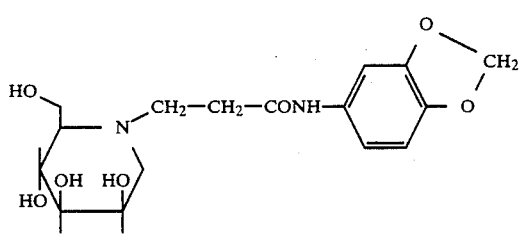

In accordance with the description for Example 1, 8.5 mmol of N-(2-carboxyethyl)-1-desoxymannonojirimycin are reacted with 10 mmol of 3,4-methylenedioxyaniline.

$R_f = 0.62$.

$[\alpha]_D^{20} = -43°$ (c=1.0, methanol).

Example 73

N-(2-Methylthiophenyl)-3-(1,5-didesoxy-1,5-imino-D-mannit-N-yl)propionamide

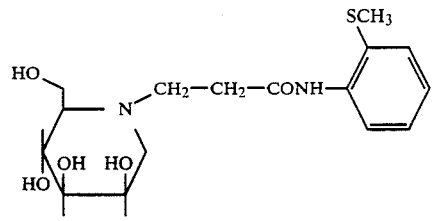

In accordance with the description for Example 1, 8.5 mmol of N-(2-carboxyethyl)-1-desoxymannonojirimycin are reacted with 10 mmol of 2-methylthioaniline.

$R_f = 0.68$.

$[\alpha]_D^{20} = -50°$ (c=1.0, methanol).

Example 74

3-(1,5-Didesoxy-1,5-imino-D-mannit-N-yl)-propionyl-4-(4-trifluoromethylphenyl)piperazine

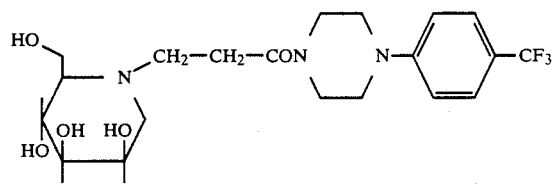

In accordance with the description for Example 1, 8.5 mmol of N-(2-carboxyethyl)-1-desoxymannonojirimycin are reacted with 10 mmol of 1-(4-trifluoromethylphenyl)piperazine.

$R_f = 0.67$.

Example 75

N-Phenyl-3-(1,5-didesoxy-1,5-imino-D-mannit-N-yl)propionamide

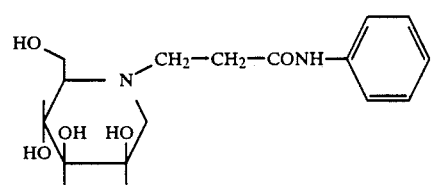

In accordance with the description for Example 1, 8.5 mmol of N-(2-carboxyethyl)-1-desoxymannonojirimycin are reacted with 10 mmol of aniline.

$R_f = 0.52$.

Example 76

N-(4-Ethoxyphenyl)-3-(1,5-didesoxy-1,5-imino-D-mannit-N-yl)propionamide

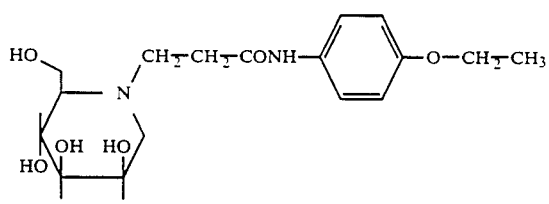

In accordance with the description for Example 1, 8.5 mmol of N-(2-carboxyethyl)-1-desoxymannonojirimycin are reacted with 10 mmol of 4-ethoxyaniline.
$R_f=0.52$.
$[\alpha]_D^{20} = -46°$ (c=1.0, methanol).

Example 77

N-2-Dimethylaminoethyl-3-(1,5-didesoxy-1,5-imino-D-mannit-N-yl)-propionamide

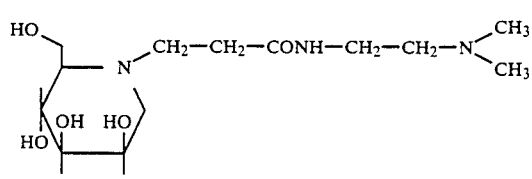

In accordance with the description for Example 1, 8.5 mmol of N-(2-carboxyethyl)-1-desoxymannonojirimycin are reacted with 10 mmol of 2-dimethylaminoethylamine.
$R_f=0.59$.

Example 78

N-[2-(3-Methoxyphenyl)ethyl]-3-(1,5-didesoxy-1,5-imino-D-mannit-N-yl)propionamide

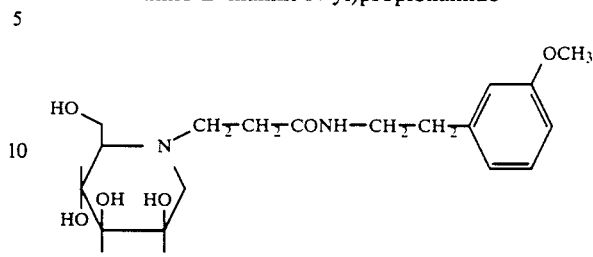

In accordance with the description for Example 1, 8.5 mmol of N-(2-carboxyethyl)-1-desoxymannonojirimycin are reacted with 10 mmol of 2-(3-methoxyphenyl)ethylamine. $R_f=0.61$.

Example 79

N-(2-Pyridylmethyl)-3-(1,5-didesoxy-1,5-imino-D-mannit-N-yl)propionamide

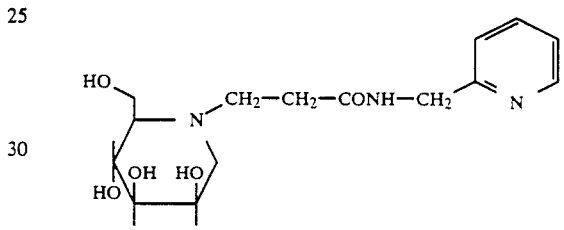

In accordance with the description for Example 1, 8.5 mmol of N-(2-carboxyethyl)-1-desoxymannonojirimycin are reacted with 10 mmol of 2-aminomethylpyridine.
$R_f=0.51$.
$[\alpha]_D^{20} = -15$ (c=1.0, methanol).

Example 80

3-(1,5-Didesoxy-1,5-imino-D-mannit-N-yl)-propionyl-(4-cinnamyl)piperazine

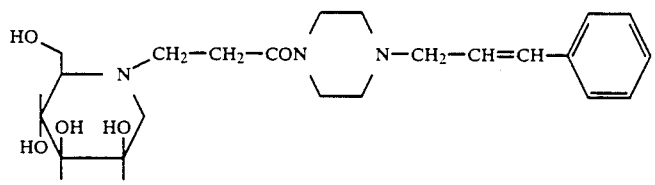

In accordance with the description for Example 1, 8.5 mmol of N-(2-carboxyethyl)-1-desoxymannonojirimycin are reacted with 10 mmol of 1-cinnamylpiperazine.
$R_f=0.67$.

Example 81

N-[4-(2-hydroxyethoxy)phenyl]-3-(1,5-didesoxy-1,5-imino-D-mannit-N-yl)propionamide

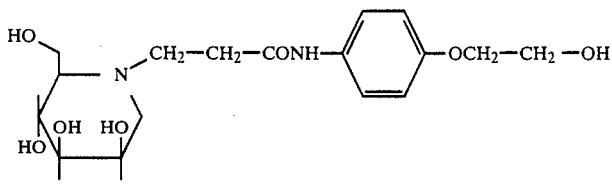

In accordance with the description for Example 1, 8.5 mmol of N-(2-carboxyethyl)-1-desoxymannonojirimycin are reacted with 10 mmol of 4-(2-hydroxyethoxy)aniline.

$R_f = 0.43$.

Example 82

3-(1,5-Didesoxy-1,5-imino-D-mannit-N-yl)-propionyl-1-(4-p-fluorophenyl)piperazine

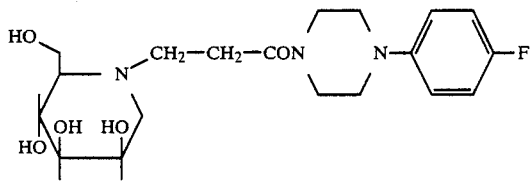

In accodance with the description for Example 1, 8.5 mmol of N-(2-carboxyethyl)-1-desoxymannonojirimycin are reacted with 10 mmol of 4-fluorophenyl)piperazine.

$R_f = 0.64$.
$[\alpha]_D^{20} = -23°$ (c=1.0, methanol).

Example 83

3-(1,5-Didesoxy-1,5-imino-D-mannit-N-yl)propionitrile

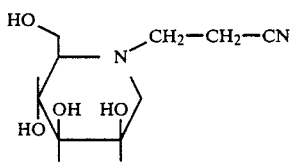

326.4 g (2 mol) of 1-desoxymannonojirimycin are dissolved in 5 l of an 0.1M aqueous potassium hydrogen phosphate solution and as much 1N sodium hydroxide solution is added as is necessary to give a pH of 7.5. 80 ml of acrylonitrile are added to the solution. This mixture is stirred at 50° C. for 48 hours. After this time, the educt can no longer be detected. (Thin-layer chromatography: CH$_2$Cl$_2$:MeOH:NH$_3$ solution=4:3:1, $R_f = 0.4$). For working up, reagent and solvent are evaporated in high vacuum, the residue is taken up in 5 l of a mixture of pyridine aand acetic anhydride in the ratio 2:1 and stirred for 8 hours. After evaporating the solvent, the residue is taken up in 3 l of chloroform, and the solution is extracted repeatedly with water, dried over sodium sulphate and concentrated again. A syrup is obtained which is chromatographed on 2 kg of silica gel 60 in the system CH$_2$Cl$_2$:EtOH=60:1. After evaporation of the eluent, the residue is taken up in 3 l of anhydrous methanol to which 0.1% sodium methoxide is added. After 8 hours at 40° C., the deblocking reaction has proceeded to completion. The mixture is neutralized by the addition of 50 g of a strongly acidic ion exchanger, filtered off and concentrated slowly. 362 g (84%) of product crystallize.

$R_f = 0.4$.
$[\alpha]_D^{20} = -59°$ (c=1.0, methanol).

Example 84

3-(1,5-Didesoxy-1,5-imino-D-mannit-N-yl)propionic acid

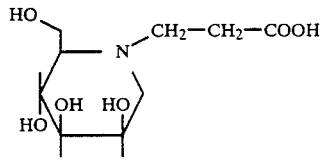

50 g (0.23 mol) of the compound from Example 83 are dissolved in 1000 ml of water, 8 g of barium hydroxide are added and the mixture is stirred for 120 minutes at 80° C. After cooling, the mixture is rendered neutral by the addition of 2N sulphuric acid. The precipitate is separated off by centrifuging and 44.4 g (82%) of product are isolated after evaporation of the solvent.

$R_f = 0.1$.
$[\alpha]_D^{20} = -41°$ (c=1, H$_2$O).

Example 85

3-(1,5-Didesoxy-1,5-imino-D-glucit-N-yl)-propionyl-1-(4-phenyl)piperazine

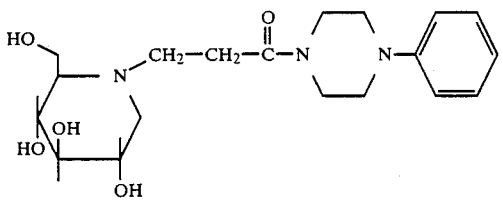

In accordance with the description for Example 1, 8.5 mmol of N-(2-carboxyethyl)desoxynojirimycin are reacted with 10 mmol of 1-phenylpiperazine.

$R_f = 0.65$.

Example 86

3-(1,5-Didesoxy-1,5-imino-D-glucit-N-yl)-propionyl-1-(4-cyclopropyl)piperazine

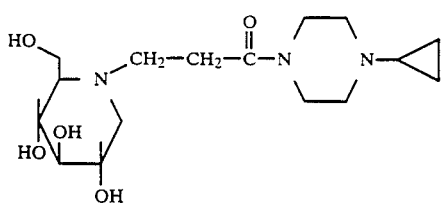

In accordance with the description for Example 1, 8.5 mmol of N-(2-carboxyethyl)desoxynojirimycin are reacted with 10 mmol of 1-cyclopropylpiperazine.
$R_f$ 0.6.

Example 87

3-(1,5-Didesoxy-1,5-imino-D-glucit-N-yl)-propionyl-1-(4-tolyl)piperazine

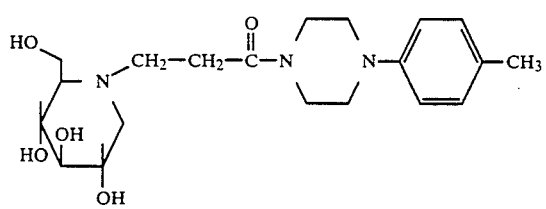

In accordance with the description for Example 1, 8.5 mmol of N-(2-carboxyethyl)desoxynojirimycin are reacted with 10 mmol of 1-(4-methylphenyl)piperazine.
$R_f$ 0.66.

Example 88

3-(1,5-Didesoxy-1,5-imino-D-glucit-N-yl)propionyl-1-(4-[2-pyrrolyl-2-ketoethyl])piperazine

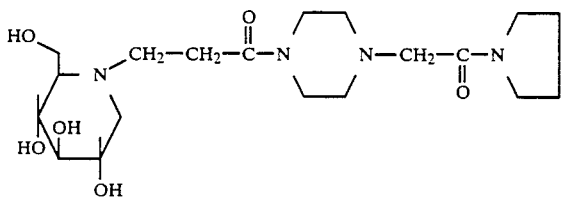

In accordance with the description for Example 1, 8.5 mmol of N-(2-carboxyethyl)desoxynojirimycin are reacted with 10 mmol of N-pyrrolyl piperazinoacetamide.
$R_f$ 0.65.

Example 89

N-(4-Trifluoromethylbenzyl)-3-(1,5-didesoxy-1,5-imino-D-glucit-N-yl)propionamide

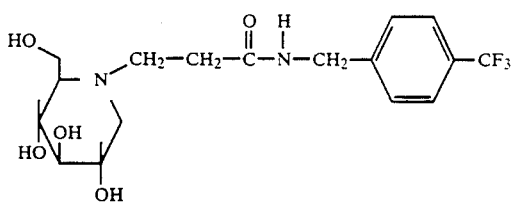

In accordance with the description for Example 1, 8.5 mmol of N-(2-carboxyethyl)desoxynojirimycin are reacted with 10 mmol of 4-trifluoromethylbenzylamine.
$R_f$ 0.65.

Example 90

N-(2-Phenyl)-2-ketoethyl)-3-(1,5-didesoxy-1,5-imino-D-glucit-N-yl)propionamide

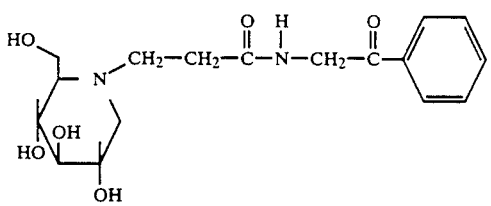

In accordance with the description for Example 1, 8.5 mmol of N-(2-carboxyethyl)desoxynojirimycin are reacted with 10 mmol of β-aminoacetophenone.
$R_f$ 0.59.

Example 91

N-(Quinuclidin-3-yl)-3-(1,5-didesoxy-1,5-imino-D-glucit-N-yl)propionamide

In accordance with the description for Example 1, 8.5 mmol of N-(2-carboxyethyl)desoxynojirimycin are reacted with 10 mmol of 3-aminoquinuclidine.
$R_f$ 0.65.

Example 92

3-(1,5-Didesoxy-1,5-imino-D-glucit-N-yl)propionyl-1-(4-2-fluorophenyl)piperazine

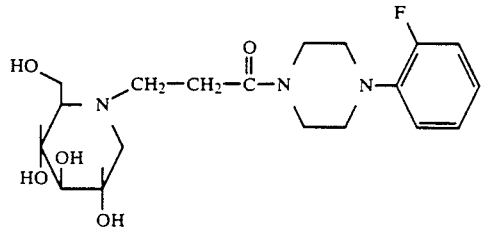

In accordance with the description for Example 1, 8.5 mmol of N-(2-carboxyethyl)desoxynojirimycin are reacted with 10 mmol of 1-(2-fluorophenyl)piperazine.
R$_f$ 0.7.

Example 93

3-(1,5-Didesoxy-1,5-imino-D-glucit-N-yl)propionyl-1-(3-methylphenyl)piperazine

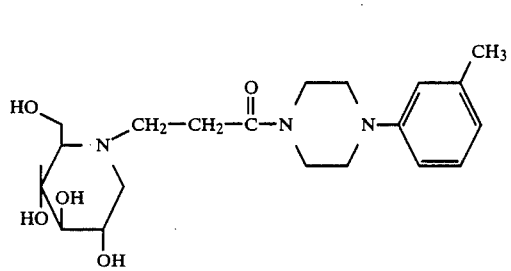

In accordance with the description for Example 1, 8.5 mmol of N-(2-carboxyethyl)desoxynojirimycin are reacted with 10 mmol of 1-(3-methylphenyl)piperazine.
R$_f$ 0.65.

Example 94

3-(1,5-Didesoxy-1,5-imino-D-glucit-N-yl)propionyl-1-(4-2-nitrophenyl)piperazine

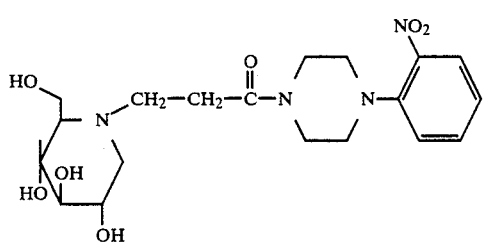

In accordance with the description for Example 1, 8.5 mmol of N-(2-carboxyethyl)desoxynojirimycin are reacted with 10 mmol of 1-(2-nitrophenyl)piperazine.
R$_f$ 0.65.

Example 95

3-(1,5-Didesoxy-1,5-imino-D-glucit-N-yl)propionyl-1-(4-2-cyanophenyl)piperazine

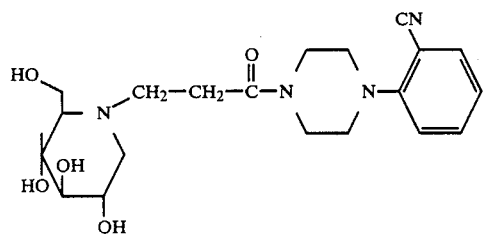

In accordance with the description for Example 1, 8.5 mmol of N-(2-carboxyethyl)desoxynojirmycin are reacted with 10 mmol of 1-(2-cyanophenyl)piperazine.
R$_f$ 0.65.

Example 96

3-(1,5-Didesoxy-1,5-imino-D-glucit-N-yl)propionyl-1-(4-2-methylphenyl)piperazine

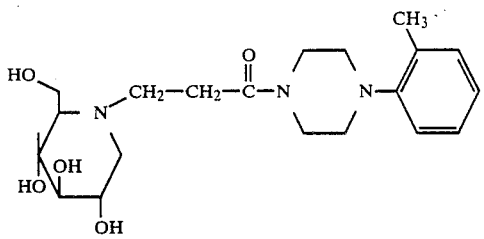

In accordance with the description for Example 1, 8.5 mmol of N-(2-carboxyethyl)desoxynojirimycin are reacted with 10 mmol of 1-(2-methylphenyl)piperazine.
R$_f$ 0.6.

Example 97

3-(1,5-Didesoxy-1,5-imino-D-glucit-N-yl)propionyl-1-(4-[3-trifluoromethyl-4-chlorophenyl])piperazine

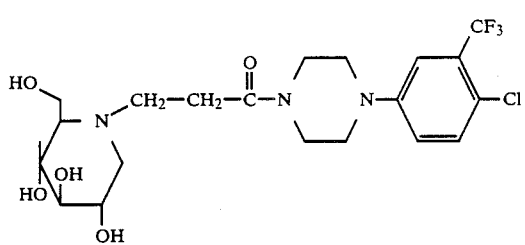

In accordance with the description for Example 1, 8.5 mmol of N-(2-carboxyethyl)-desoxynojirimycin are reacted with 10 mmol of 1-(3-trifluoromethyl)-4-chlorophenyl)piperazine
R$_f$ 0.65.

Example 98

3-(1,5-Didesoxy-1,5-imino-D-glucit-N-yl)propionyl-1-(4-[2-morpholino-2-ketoethyl])piperazine

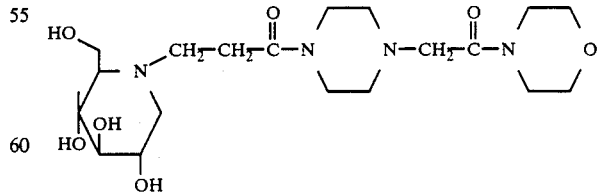

In accordance with the description for Example 1, 8.5 mmol of N-(2-carboxyethyl)desoxynojirimycin are reacted with 10 mmol of piperazinoacetomorpholine.
R$_f$ 0.66.

Example 99

3-(1,5-Didesoxy-1,5-imino-D-glucit-N-yl)-propionyl-1-(4-[2-pyrimidyl])piperazine

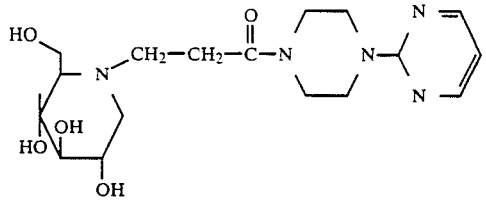

In accordance with the description for Example 1, 8.5 mmol of N-(2-carboxyethyl)desoxynojirimycin are reacted with 10 mmol of 1-(2-pyrimidyl)piperazine.
$R_f$ 0.65.

Example 100

3-(1,5-Didesoxy-1,5-imino-D-glucit-N-yl)propionyl-1-thiomorpholide

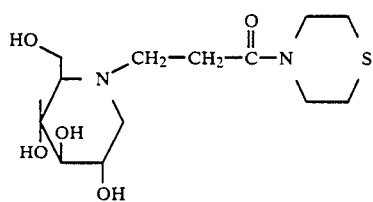

In accordance with the description for Example 1, 8.5 mmol of N-(2-carboxyethyl)desoxynojirimycin are reacted with 10 mmol of thiomorpholine.
$R_f$ 0.6.

Example 101

N-[(Thiophen-2-yl)-methyl]-3-(1,5-didesoxy-1,5-imino-D-glucit-N-yl)propionamide

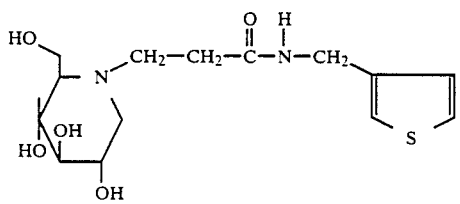

In accordance with the description for Example 1, 8.5 mmol of N-(2-carboxyethyl)desoxynojirimycin are reacted with 10 mmol of 2-aminomethylthiophene.
$R_f$ 0.59.

Example 102

N-[(1S)-1-Phenethyl]-3-(1,5-didesoxy-1,5-imino-D-glucit-N-yl)propionamide

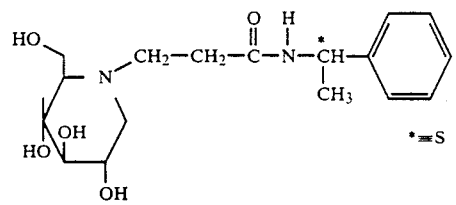

In accordance with the description for Example 1, 8.5 mmol of N-(2-carboxyethyl)desoxynojirimycin are reacted with 10 mmol of L(−)-1-phenethylamine.
$R_f$ 0.65.

Example 103

N-[(1R)-phenethyl)]-3-(1,5-didesoxy-1,5-imino-D-glucit-N-yl)propionamide

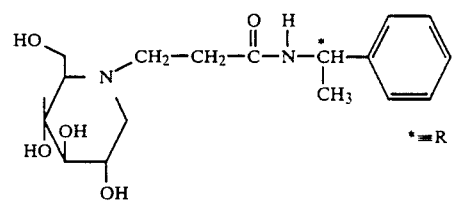

In accordance with the description for Example 1, 8.5 mmol of N-(2-carboxyethyl)desoxynojirimycin are reacted with 10 mmol of D(+)-1-phenethylamine.
$R_f$ 0.65.

Example 104

N-Butyl-3-(1,5-didesoxy-1,5-imino-D-glucit-N-yl)propionamide

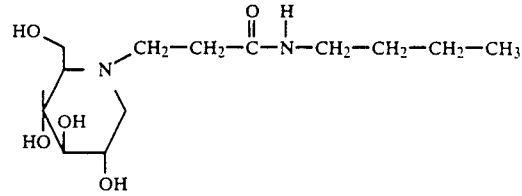

In accordance with the description for Example 1, 8.5 mmol of N-(2-carboxyethyl)desoxynojirimycin are reacted with 10 mmol of butylamine.
$R_f$ 0.62.

Example 105

N-t-Butyl-3-(1,5-didesoxy-1,5-imino-D-glucit-N-yl)propionamide

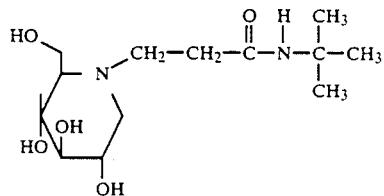

In accordance with the description for Example 1, 8.5 mmol of N-(2-carboxyethyl)desoxynojirimycin are reacted with 10 mmol of t-butylamine.

$R_f$ 0.6.

Example 106

N-(4-Decyloxyphenyl)-3-(1,5-didesoxy-1,5-imino-D-glucit-N-yl)propionamide

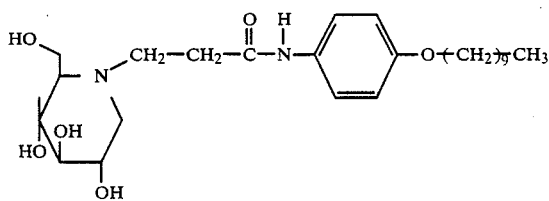

In accordance with the description for Example 1, 8.5 mmol of N-(2-carboxyethyl)desoxynojirimycin are reacted with 10 mmol of 4-decyloxyaniline.

$R_f$ 0.8.

Example 107

4-(1,5-Didesoxy-1,5-imino-D-glucit-N-yl)butanoic acid

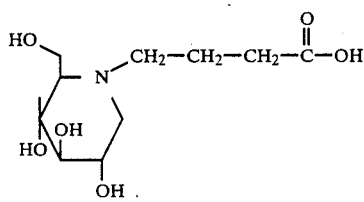

$R_f$ 0.25 $CH_2Cl_2$:MeOH:$NH_3$ solution.

Example 108

N-(4-Ethoxyphenyl)-4-(1,5-didesoxy-1,5-imino-D-glucit-N-yl)butanamide

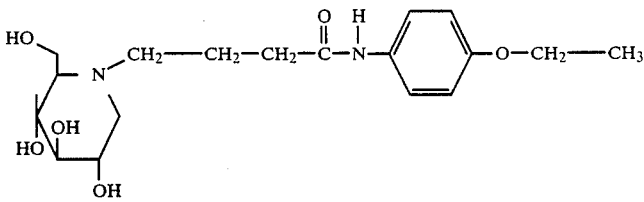

In accordance with the description for Example 1, 8.5 mmol of N-(3-carboxypropyl)desoxynojirimycin are reacted with 10 mmol of 4-ethoxyaniline.

$R_f$ 0.68.

Example 109

N-(4-t-Butylphenyl)-4-(1,5-didesoxy-1,5-imino-D-glucit-N-yl)butanamide

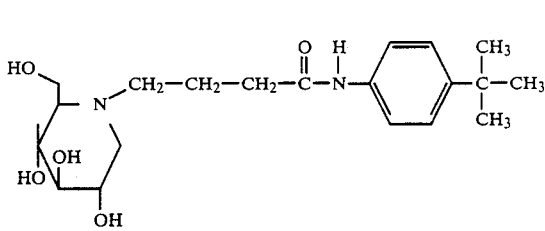

In accordance with the description for Example 1, 8.5 mmol of N-(3-carboxyphenyl)desoxynojirimycin are reacted with 10 mmol of 4-t-butylaniline.

$R_f$ 0.6.

Example 110

N-[4-(2-Chloro-1,1,2-trifluoroethoxy)phenyl]-4-(1,5-didesoxy-1,5-imino-D-glucit-N-yl)butanamide

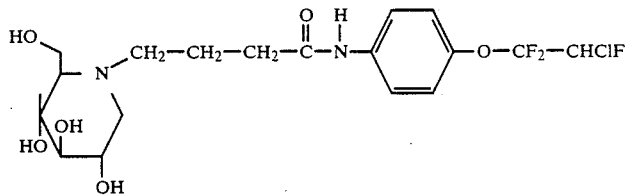

1 mol of 1-desoxynojirimycin is dissolved in 1 l of N,N-dimethylformamide, 0.5 mol of potassium carbonate is added and the 1.0 mol of ethyl ω-bromo-butanoate is added dropwise to this suspension with stirring. As soon as no more evolution of gas can be observed, the mixture is filtered off from the solid material and concentrated. The residue is taken up in 1.05 l of 1N sodium hydroxide solution and stirred at 90° C. for 8 hours. The solution is then stirred with 1000 ml of a strongly acidic ion exchanger and filtered off.

After evaporating the solvents, 0.75 mol of product is isolated.

In accordance with the description for Example 1, 8.5 mmol of N-(3-carboxypropyl)desoxynojirimycin are reacted with 10 mmol of 4-(2-chloro-1,1,2-trifluoroethoxy)aniline.

$R_f$ 0.65.

Example 111

N-(4-Cyclohexylphenyl)-4-(1,5-didesoxy-1,5-imino-D-glucit-N-yl)butanamide

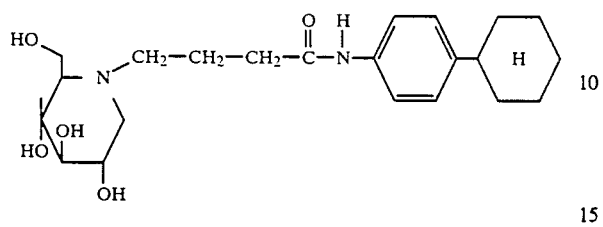

In accordance with the description for Example 1, 8.5 mmol of N-(3-carboxypropyl)desoxynojirimycin are reacted with 10 mmol of 4-cyclohexylaniline. $R_f$ 0.7.

Example 112

1-[3-(1,5-Didesoxy-1,5-imino-D-glucit-N-yl)propionyl]-1,2,3,4-tetrahydroisoquinoline

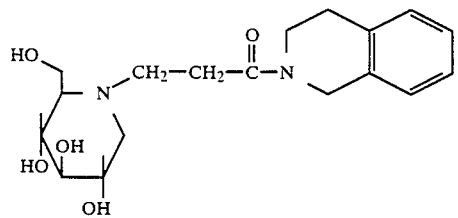

In accordance with the description for Example 1, 8.5 mmol of N-(2-carboxyethyl)-desoxynojirimycin are reacted with 10 mmol of 1,2,3,4-tetrahydroisoquinoline. $R_f$ 0.65.

Example 113

2-[1,5-didesoxy-1,5-imino-D-glucit-N-yl]ethane-methylate

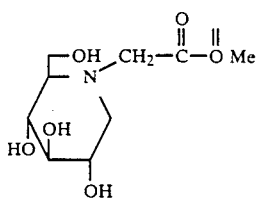

To a suspension of 163 g (1 mol) 1-desoxynojirimycin in 2000 ml of dry N,N-dimethylformamide, 69,1 g (0.5 mol) potassiumcarbonate were added. The suspension was cooled to 0° and 153 g (1 mol) of 2-bromo-methylacetate were added over a period of 1 hour.

The reaction mixture was stirred at 0° for a further 10 hours. For workup the salts then were separated off by filtration with suction and the solvent was evaporated. The crude product was directly submitted to the next reaction step.

$R_f$ 0.6. $CH_2Cl_2$ MeOH $H_3N$ =4:3:1 vvv.

Example 114

N-Phenyl-2-(1,5-didesoxy-1,5-imino-D-glucit-N-yl)ethaneamide

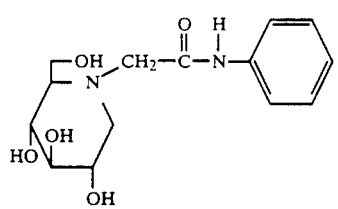

23.5 g (0,1 mol) of the compound described in Example 113 and 9.3 g (0,1 mol) of freshly distilled aniline were heated for five hours to 180° under an atmosphere of inert gas.

After that time the reaction product was absorbed on silica gel and purified by chromatography with Toluene=Ethanol=40:1 1:1 as the eluent.

$R_f$ 0.45.

Example 115

N-(4-Ethoxyphenyl)-2-(1,5-didesoxy-1,5-imino-D-glucit-N-yl) ethaneamide

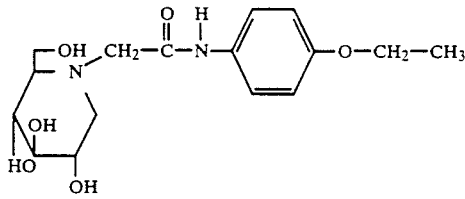

In accordance with the description for Example 114 0.1 mol of 2-(1,5-didesoxy-1,5-imino-D-glucit-N-yl) ethanemethylate are reacted with 0.1 mol of 4-ethoxyamiline.

$R_f$ 0.45.

Example 116

N-(4-Tert.-butylphenyl)-2-(1,5-didesoxy-1,5-imino-D-glucit-N-yl)ethaneamide

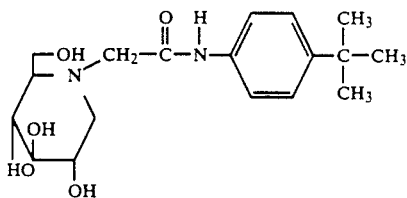

In accordance with the description for Example 114 0.1 mol of 2-(1,5-didesoxy-1,5-imino-D-glucit-N-yl) ethanemethylate are reacted with 0.1 mol of 4-tert.-butylaniline.

$R_f$ 0.6.

Example 117

N-[4-(2-Hydroxyethoxy)phenyl]-2-(1,5-didesoxy-1,5-imino-D-glucit-N-yl)ethaneamide

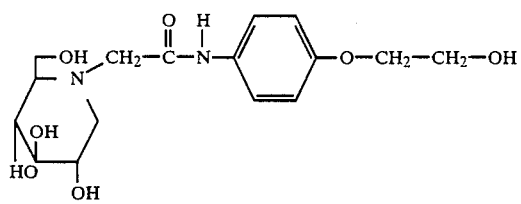

In accordance with the description for Example 114 0.1 mol of 2-(1,5-didesoxy-1,5-imino-D-glucit-N-yl) ethanemethylate are reacted with 0.1 mol of 4-(2-Hydroxyethoxy)-aniline.

$R_f$ 0.35.

Example 118

N-(4-Hydroxyphenyl)-2-(1,5-didesoxy-1,5-imino-D-glucit-N-yl)ethaneamide

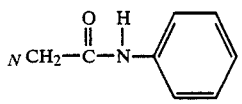

In accordance with the description for Example 114 0.1 mol of 2-(1,5-didesoxy-1,5-imino-D-glucit-N-yl) ethanemethylate are reacted with 0.1 mol of 4-hydroxyaniline.

$R_f$ 0.55.

What is claimed is:

1. A compound of the formula

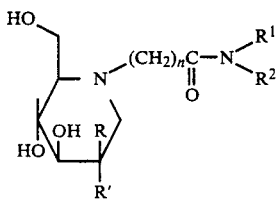

in which

R or R' stands for a hydroxyl group and in which the other R' or R in each case stands for hydrogen, n stands for a number from 1 to 6, $R^1$
stands for hydrogen, or
for straight-chain or branched alkyl having up to 3 carbon atoms or for benzyl, and $R^2$
stands for straight-chain or branched alkyl having up to 8 carbon atoms which is substituted by aryl having 6 to 10 carbon atoms, where the aryl is radical is unsubstituted or substituted by up to 4 identical or different substituents selected from the group consisting of fluorine; chlorine; bromine; iodine; cyano; nitro; alkyl, alkoxy, alkylthio and arylthio each having up to 6 carbon atoms; dioxymethylene; dioxyethylene; trifluoromethyl; trifluoromethoxy; difluoromethoxy; carboxyl and alkoxycarbonyl having up to 4 carbon atoms, or which can be substituted by pyridyl; thienyl; furyl; pyrimidyl; pyridazinyl; pyrazinyl or quinolyl,
or
stands for cycloalkyl having 3 to 7 carbon atoms,
or
stands for aryl having 6 to 10 carbon atoms, where the aryl radical is unsubstituted or monosubstituted to tetrasubstituted by fluorine, chlorine, bromine, iodine, cyano, alkyl having up to 6 carbon atoms, alkoxy having up to 12 carbon atoms, alkylsulphonyl having up to 4 carbon atoms, trifluoromethyl, difluoromethylene, trifluoromethylthio, dioxymethylene, dioxyethylene, by cycloalkyl having 3 to 7 carbon atoms, by carboxyl or alkoxycarbonyl having up to 4 carbon atoms, by aryloxy having 6 to 10 carbon atoms, where the aryl radical of the aryloxy is unsubstituted or is substituted by up to 4 identical or different substitutents selected from the group consisting of fluorine; chlorine; bromine; iodine, cyano, hydroxyl; nitro; alkyl, alkoxy, alkylthio having up to 6 carbon atoms; dioxymethylene; dioxyethylene; trifluoromethyl; trifluoromethoxy; or difluoromethoxy; or by halogenoalkoxy having up to 6 carbon atoms and up to 5 fluorine and/or 3 chlorine atoms; or by hydroxyalkoxy, hydroxyalkyl and cyanoalkyl each having up to 8 carbon atoms; and alkenyloxy having up to 6 carbon atoms; or by a group —$XR^3$, the substituents being identical or different, where X denotes a straight-chain or branched alkylene or alkenylene chain having up to 8 carbon atoms, and $R^3$ denotes aryl having 6 to 10 carbon atoms, where
the aryl radical is unsubstitued or substituted by up to 4 identical or different substituents selected from the group consisting of fluorine; chlorine; bromine; iodine; cyano; alkyl, alkoxy, alkylthio having up to 6 carbon atoms; nitro; dioxymethylene; dioxyethylene; trifluoromethyl; trifluoromethoxy; difluoromethoxy; and trifluoromethylthio, or $R^3$ denotes a 5- or 6-membered saturated or unsaturated heterocyclic ring which can be fused to benzene and which can contain oxygen, sulphur or up to 2 nitrogen atoms as hetero atoms, or denotes hydroxyl, carboxyl, alkoxycarbonyl having up to 6 carbon atoms, alkylcarbonyloxy having up to 18 carbon atoms, or $R^3$ denotes a group —$OSO_3H$, —$CONH$—$NH_2$, —$CONH_2$, amino or alkylamino or dialkylamino each having up to 6 carbon atoms per alkyl group, or $R^3$ denotes hydroxyalkyl having up to 8 carbon atoms, or $R^3$ denotes a saturated, bridged heterocycle or $R^1$ and $R^2$, together with the nitrogen atom, form a 5- to 6-membered ring which can be anellated, which can be interrupted by oxygen, sulphur or the group —$NR^4$, and which can be substituted by alkyl having up to 4 carbon atoms, hydroxyl, phenyl, carboxyl or alkoxycarbonyl having up to 4 carbon atoms, where $R^4$
denotes aryl having 6 to 10 carbon atoms, where the aryl radical is unsubstituted or substituted by up to 4 identical or different substituents selected from the group consisting of fluorine; chlorine; bromine; iodine; cyano; nitro; hydroxyl; alkyl, alkoxy, alkylthio having up to 6 carbon atoms; dioxymethylene; dioxyethylene; trifluoromethyl; trifluoromethoxy and difluoromethoxy, or R⁴ denotes alkoxycarbonyl having up to 6 carbon atoms, or R⁴ denotes pyridyl, pyrimidyl, furyl, thienyl, pyrazinyl, pyridazinyl or quinolyl, or R⁴ denotes cycloalkyl having 3 to 7 carbon atoms, or R⁴ denotes alkyl or alkenyl having up to 6 carbon atoms which is unsubstituted or monosubstituted or disubstituted by phenyl which is unsubstituted or substituted by chlorine, dioxymethylene or trifluoromethyl, hydroxyl, amino, alkylamino, dialkylamino each having up to 3 carbon atoms per alkyl group, fluorine, bromine, cycloalkyl having 3 to 6 carbon atoms, by carboxyl or alkoxycarbonyl having up to 6 carbon atoms, by pyridyl, pyrimidyl, pyrazinyl, morpholinyl, thiomorpholinyl, pyrrolidinyl or pyrrolidinocarbonyl, by morpholinocarbonyl, by alkylaminocarbonyl, dialkylaminocarbonyl or phenylalkylaminocarbonyl each having up to 6 carbon atoms per alkyl group, the substituents being identical or different.

2. A compound according to claim 1, where
n stands for the numbers 1 to 4,
R¹ stands for hydrogen, and
R²
stands for straight-chain or branched alkyl having up to 6 carbon atoms, which is substituted by pyridyl, thienyl or by phenyl, where the phenyl radical is unsubstituted or substituted by up to 3 identical or different substituents selected from the group consisting of fluorine; chlorine; bromine; hydroxyl; alkyl, alkoxy having up to 4 carbon atoms; dioxymethylene; dioxyethylene and carboxyl, or R²
stands for cyclopentyl, cyclohexyl or cycloheptyl, or R²
stands for phenyl which is unsubstituted or monosubstituted, disubstituted or trisubstituted by fluorine; chlorine; bromine; cyano; alkyl having up to 4 carbon atoms; hydroxyalkyl or hydroxyalkoxy having up to 4 carbon atoms; trifluoromethyl; trifluoromethoxy; dioxymethylene; dioxyethylene; by phenyl which is unsubstituted or substituted in the aromatic part by fluorine; chlorine; bromine; hydroxyl; alkyl, alkoxy having up to 9 carbon atoms; dioxymethylene; trifluoromethyl or carboxyl, or by straight-chain or branched alkenyloxy having up to 4 carbon atoms, or by a group —XR³, the substituents being identical or different,
where
X
denotes a straight-chain or branched alkylene chain having up to 6 carbon atoms and
R³
denotes phenyl which is monosubstituted, disubstituted or trisubstituted by fluorine; chlorine; bromine; hydroxyl; alkyl, alkoxy having up to 4 carbon atoms; dioxymethylene; trifluoromethyl or carboxyl, the substituents being identical or different, or R³
denotes pyridyl, morpholinyl or piperidinyl, or R³
denotes hydroxyl, carboxyl, alkoxycarbonyl having up to 4 carbon atoms, or cyclopropyl, cyclopentyl or cyclohexyl or R³ denotes amino, alkylamino or dialkylamino each having up to 4 carbon atoms per alkyl group,
R¹ and R², together with the nitrogen, form a ring of the formula

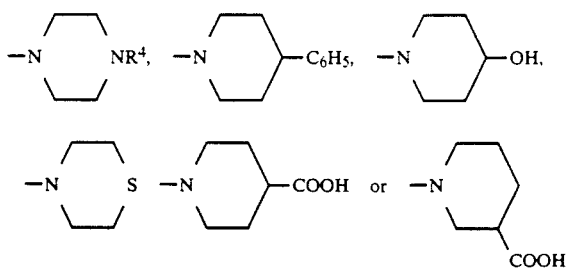

where
R⁴
denotes phenyl which is unsubstituted or substituted, disubstituted or trisubstituted by fluorine; chlorine; bromine; hydroxyl; alkyl, alkoxy having up to 4 carbon atoms; dioxymethyl; trifluoromethyl or carboxyl, the substituents being identical or different, or R⁴ denotes alkoxycarbonyl having up to 4 carbon atoms, or R⁴ denotes pyridyl or pyrimidyl, or R⁴ denotes cyclopropyl, cyclopentyl or cyclohexyl, or R⁴ denotes straight-chain or branched alkyl or alkenyl having up to 4 carbon atoms, which is unsubstituted or monosubstituted or disubstituted by phenyl which is unsubstituted or substituted by chlorine, trifluoromethyl or dioxymethylene, hydroxyl, amino, methylamino, dimethylamino, fluorine, chlorine, cyclopropyl, cyclopentyl, cyclohexyl or alkoxycarbonyl having up to 4 carbon atoms, by morpholinyl or pyrrolidinyl, or by morpholinocarbonyl, dialkylamino or phenylalkylamino each having up to 4 carbon atoms, the substituents being identical or different.

3. A compound according to claim 1,
in which
n stands for the number 2,
R¹ stands for hydrogen, and
R² stands for straight-chain or branched alkyl having up to 3 carbon atoms, which is substituted by thienyl or phenyl, or R²
stands for phenyl which is unsubstituted or monosubstituted, disubstituted or trisubstituted by fluorine, chlorine, bromine, cyano, alkyl having up to 4 carbon atoms, hydroxyalkyl, alkoxy having up to 9 carbon atoms, hydroxyalkoxy having up to 4 carbon atoms, alkylthio having up to 4 carbon atoms, trifluoromethyl or trifluoromethoxy, the substituents being identical of different, or R²
stands for quinulidinyl or for 1,2,3,4-tetrahydroisoquinoline
R¹ and R², together with the nitrogen, form a ring of the formula

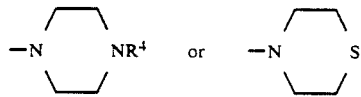

where
R⁴ denotes phenyl which is unsubstituted or monosubstituted or disubstituted by fluorine; chlorine; bromine; hydroxyl; alkyl or alkoxy having up to 4 carbon atoms, the substituents being identical or different, or $R^4$ denotes alkoxycarbonyl having up to 4 carbon atoms, or $R^4$ denotes cyclopropyl, cyclopentyl or cyclohexyl, or $R^4$ denotes straight-chain or branched alkyl or alkenyl having up to 4 carbon atoms, which is unsubstituted or monosubstituted or disubstituted by chlorine, trifluoromethyl or dioxymethylene, by hydroxyl, amino, dimethylamino, cyclopropyl or alkoxycarbonyl having up to 4 carbon atoms, by morpholinyl, pyrrolidinyl or pyrrolidinocarbonyl, the substituents being identical or different.

4. A compound according to claim 1 selected from the group consisting of

N-(4-methoxyphenyl)-3-(1,5-didesoxy-1,5-imino-D-glucit-N-yl)propionamide,

N-(4-methoxycarbonylphenyl)-3-(1,5-didesoxy-1,5-imino-D-glucit-N-yl)propionamide, N-[4-(4-pyridylmethoxyphenyl)]-3-(1,5-didesoxy-1,5-imino-D-glucit-N-yl)propionamide, N-(4-benzyloxyphenyl)-3-(1,5-didesoxy-1,5-imino-D-glucit-N-yl)propionamide, N-(4-trifluoromethoxyphenyl)-3-(1,5-didesoxy-1,5-imino-D-glucit-N-yl)propionamide, N-(4-oxocyclohexyloxyphenyl)-3-(1,5-didesoxy-1,5-imino-D-glucit-N-yl)propionamide, N-(4-tert.-butylphenyl)-3-(1,5-didesoxy-1,5-imino-D-glucit-N-yl)propionamide, N-[4-(6-methylheptyloxy)phenyl]-3-(1,5-didesoxy-1,5-imino-D-glucit-N-yl)propionamide, N-[4-(2-N,N-diethylaminoethoxy)phenyl]-3-(1,5-didesoxy-1,5-imino-D-glucit-N-yl)propionamide, N-(4-allyloxyphenyl)-3-(1,5-didesoxy-1,5-imino-D-glucit-N-yl)propionamide, N-(4-trifluoromethylphenyl)-3-(1,5-didesoxy-1,5-imino-D-glucit-N-yl)propionamide, N-[4-(2-chloro-1,1,2-trifluoromethoxy)phenyl]-3-(1,5-didesoxy-1,5-imino-D-glucit-N-yl)propionamide, N-(4-hydroxyphenyl)-3-(1,5-didesoxy-1,5-imino-D-glucit-N-yl)propionamide, N-(4-isopropylphenyl)-3-(1,5-didesoxy-1,5-imino-D-glusit-N-yl)propionamide, N-(2-isopropylphenyl)-3-(1,5-didesoxy-1,5-imino-D-glucit-N-yl)propionamide, N-(4-fluorophenyl)-3-(1,5-didesoxy-1,5-imino-D-glucit-N-yl)propionamide, N-(2-fluorophenyl)-3-(1,5-didesoxy-1,5-imino-D-glucit-N-yl)propionamide, 1-[3-(1,5-didesoxy-1,5-imino-D-glucit-N-yl)-propionyl]-2,3-dihydroindole, N-(2,4-difluorophenyl)-3-(1,5-didesoxy-1,5-imino-D-glucit-N-yl)propionamide, N-(2-trifluoromethylphenyl)-3-(1,5-didesoxy-1,5-imino-D-glucit-N-yl)propionamide, N-(2,6-difluorophenyl)-3-(1,5-didesoxy-1,5-imino-D-glucit-N-yl)propionamide, N-(adamantan-1-yl)-3-(1,5-didesoxy-1,5-imino-D-glucit-N-yl)propionamide, N-(3,4,5-trimethoxyphenyl)-3-(1,5-didesoxy-1,5-imino-D-glucit-N-yl)propionamide, N-(3,4-dimethoxyphenyl)-3-(1,5-didesoxy-1,5-imino-D-glucit-N-yl)propionamide, N-(3,5-dimethoxyphenyl)-3-(1,5-didesoxy-1,5-imino-D-glucit-N-yl)propionamide, N-(2,4,6-tribromophenyl)-3-(1,5-didesoxy-1,5-imino-D-glucit-N-yl)propionamide, N-(3-cyanophenyl)-3-(1,5-didesoxy-1,5-imino-D-glucit-N-yl)propionamide, N-(4-cyclohexylphenyl)-3-(1,5-didesoxy-1,5-imino-D-glucit-N-yl)propionamide, N-(3,4-ethylenedioxyphenyl)-3-(1,5-didesoxy-1,5-imino-D-glucit-N-yl)propionamide, N-(2-bromophenyl)-3-(1,5-didesoxy-1,5-imino-D-glucit-N-yl)propionamide, N-(3,4-methylenedioxyphenyl)-3-(1,5-didesoxy-1,5-imino-D-glucit-N-yl)propionamide, N-(2-methylthiophenyl)-3-(1,5-didesoxy-1,5-imino-D-glucit-N-yl)propionamide, 3-(1,5-didesoxy-1,5-imino-D-glucit-N-yl)-propionyl-4-(4-trifluoromethylphenyl)piperazine, N-phenyl-3-(1,5-didesoxy-1,5-imino-D-glucit-N-yl)-propionamide, N-(4-ethoxyphenyl)-3-(1,5-didesoxy-1,5-imino-D-glucit-N-yl)propionamide, N-(2-dimethylaminoethyl)-3-(1,5-didesoxy-1,5-imino-D-glucit-N-yl)propionamide, N-[2-(3-methoxyphenyl)ethyl]-3-(1,5-didesoxy-1,5-imino-D-glucit-N-yl)propionamide, N-(2-pyridylmethyl)-3-(1,5-didesoxy-1,5-imino-D-glucit-N-yl)propionamide, 3-(1,5-didesoxy-1,5-imino-D-glucit-N-yl)-propionyl-(4-cinnamyl)piperazine, N-[4-(2-hydroxyethoxy)phenyl]-3-(1,5-didesoxy-1,5-imino-D-glucit-N-yl)propionamide, N-(4-methoxyphenyl)-3-(1,5-didesoxy-1,5-imino-D-mannit-N-yl)propionamide, N-(4-methoxycarbonylphenyl)-3-(1,5-didesoxy-1,5-imino-D-mannit-N-yl)propionamide, N-[4-(4-pyridylmethoxy)phenyl]-3-(1,5-didesoxy-1,5-imino-D-mannit-N-yl)propionamide, N-(4-benzyloxyphenyl)-3-(1,5-didesoxy-1,5-imino-D-mannit-N-yl)propionamide, N-(4-trifluoromethoxyphenyl)-3-(1,5-didesoxy-1,5-imino-D-mannit-N-yl)propionamide, N-[4-(2-oxocyclohexyloxy)phenyl]-3-(1,5-didesoxy-1,5-imino-D-mannit-N-yl)propionamide, N-(4-tert.-butylphenyl)-3-(1,5-didesoxy-1,5-imino-D-mannit-N-yl)propionamide, N-[4-(6-methyl-heptyloxy)phenyl]-3-(1,5-didesoxy-1,5-imino-D-mannit-N-yl)propionamide, N-[4-(2-N,N-diethylaminoethoxy)phenyl]-3-(1,5-didesoxy-1,5-imino-D-mannit-N-yl)propionamide, N-(4-allyloxyphenyl)-3-(1,5-didesoxy-1,5-imino-D-mannit-N-yl)propionamide, N-(4-trifluoromethylphenyl)-3-(1,5-didesoxy-1,5-imino-D-mannit-N-yl)propionamide, N-[4-(2-chloro-1,1,2-trifluoroethoxy)phenyl]-3-(1,5-didesoxy-1,5-imino-D-mannit-N-yl)propionamide, N-(4-isopropylphenyl)-3-(1,5-didesoxy-1,5-imino-D-mannit-N-yl)propionamide, N-(2-isopropylphenyl)-3-(1,5-didesoxy-1,5-imino-D-mannit-N-yl)propionamide, N-(4-fluorophenyl)-3-(1,5-didesoxy-1,5-imino-D-mannit-N-yl)propionamide, N-(2-fluorophenyl)-3-(1,5-didesoxy-1,5-imino-D-mannit-N-yl)propionamide, 1-[3-(1,5-didesoxy-1,5-imino-D-mannit-N-yl)-propionyl]-2,3-dihydroindole, N-(2,4-difluorophenyl)-3-(1,5-didesoxy-1,5-imino-D-mannit-N-yl)propionamide, N-(2-trifluoromethylphenyl)-3-(1,5-didesoxy-1,5-imino-D-mannit-N-yl)propionamide, N-(2,6-difluorophenyl)-3-(1,5-didesoxy-1,5-imino-D-mannit-N-yl)propionamide, N-(adamantan-1-yl)-3-(1,5-didesoxy-1,5-imino-D-mannit-N-yl)propionamide, N-(3,4,5-trimethoxyphenyl)-3-(1,5-didesoxy-1,5-imino-D-mannit-N-yl)propionamide, N-(3,4-dimethoxyphenyl)-3-(1,5-didesoxy-1,5-imino-D-mannit-N-yl)propionamide, N-(3,5-dimethoxyphenyl)-3-(1,5-didesoxy-1,5-imino-D-mannit-N-yl)propionamide, N-(2,4,6-tribromophenyl)-3-(1,5-didesoxy-1,5-imino-D-mannit-N-yl)propionamide, N-(3-cyanophenyl)-3-(1,5-didesoxy-1,5-imino-D-mannit-N-yl)propionamide, N-(4-cyclohexylphenyl)-3-(1,5-didesoxy-1,5-imino-D-mannit-N-yl)propionamide, N-(3,4-ethylenedioxyphenyl)-3-(1,5-didesoxy-1,5-imino-D-mannit-N-yl)propionamide, N-(2-bromophenyl)-3-(1,5-didesoxy-1,5-imino-D-mannit-N-yl)propionamide, N-(3,4-methylenedioxyphenyl)-3-(1,5-didesoxy-1,5-imino-D-mannit-N-yl)propionamide, N-(2-methylthiophenyl)-3-(1,5-didesoxy-1,5-imino-D-mannit-N-yl)propionamide, 3-(1,5-didesoxy-1,5-imino-D-mannit-N-yl)-propionyl-4-(4-trifluoromethylphenyl)piperazine, N-phenyl-3-(1,5-didesoxy-1,5-imino-D-mannit-N-yl)-propionamide, N-(4-ethoxyphenyl)-3-(1,5-didesoxy-1,5-imino-D-mannit-N-yl)propionamide, N-(2-dimethylaminoethyl)-3-(1,5-didesoxy-1,5-imino-D-mannit-N-yl)propionamide, N-[2-(3-methoxyphenyl)ethyl]-3-(1,5-didesoxy-1,5-imino-D-mannit-N-yl)propionamide, N-(2-pyridylmethyl)-3-(1,5-didesoxy-1,5-imino-D-mannit-N-yl)propionamide, 3-(1,5-didesoxy-1,5-imino-D-mannit-N-yl)-propionyl-(4-cinnamyl)piperazine, N-[4-(2-hydroxyethoxy)phenyl]-3-(1,5-didesoxy-1,5-imino-D-mannit-N-yl)propionamide 3-(1,5-didesoxy-1,5-imino-D-mannit-N-yl-propionyl-1-(4-p-fluorophenyl)piperazine, 3-(1,5-didesoxy-1,5-imino-D-mannit-N-yl)propionitrile, 3-(1,5-didesoxy-1,5-imino-D-mannit-N-yl)propionic acid, 3-(1,5-didesoxy-1,5-imino-D-mannit-N-yl)propionyl-1-(4-phenyl)piperazine, 3-(1,5-didesoxy-1,5-imino-D-glucit-N-yl)-propionyl-1-(4-cyclopropyl)piperazine, N-(4-trifluoromethylbenzyl)-3-(1,5-imino-D-glucit-N-yl)propionamide, N-(2-phenyl-2-ketoethyl)-3-(1,5-didesoxy-1,5-imino-D-glucit-N-yl)propionamide, 3-(1,5-didesoxy-1,5-imino-D-glucit-N-yl)-propionyl-1-(4-2-fluorophenyl)piperazine, 3-(1,5-didesoxy-1,5-imino-D-glucit-N-yl)propionyl-1-(4-nitrophenyl)piperazine, 3-(1,5-didesoxy-1,5-imino-D-glucit-N-yl)propionyl-1-(4-cyanophenyl)piperazine, 3-(1,5-didesoxy-1,5-imino-D-glucit-N-yl)propionyl-1-(4-methylphenyl)piperazine, 3-(1,5-didesoxy-1,5-imino-D-glucit-N-yl)propionyl-1-(4-[3-trifluoromethyl-4-chlorophenyl])piperazine, 3-(1,5-didesoxy-1,5-imino-D-glucit-N-yl)propionyl-1-(4-[2-morpholino-2-ketoethyl])piperazine, 3-(1,5-didesoxy-1,5-imino-D-glucit-N-yl)propionyl-1-(4-[2-pyrimidyl])piperazine, 3-(1,5-didesoxy-1,5-imino-D-glucit-N-yl)propionyl-1-thiomorpholide, N-[(thiophen-2-yl)-methyl]-3-(1,5-didesoxy-1,5-imino-D-glucit-N-yl)propionamide, N-[(1S)-1-phenethyl]-3-(1,5-didesoxy-1,5-imino-D-glucit-N-yl)propionamide, N-[(1R)-phenethyl)]-3-(1,5-didesoxy-1,5-imino-D-glucit-N-yl)propionamide, N-butyl-3-(1,5-didesoxy-1,5-imino-D-glucit-N-yl)-propionamide, N-t-butyl-3-(1,5-didesoxy-1,5-imino-D-glucit-N-yl)-propionamide, N-(4-decyloxyphenyl)-3-(1,5-didesoxy-1,5-imino-D-glucit-N-yl)propionamide, N-(4-ethoxyphenyl)-4-(1,5-didesoxy-1,5-imino-D-glucit-N-yl)butanamide, N-(4-t-butylphenyl)-4-(1,5-didesoxy-1,5-imino-D-glucit-N-yl)butanamide, N-[4-(2-chloro-1,1,2-trifluoroethoxy)phenyl]-4-(1,5-didesoxy-1,5-imino-D-glucit-N-yl)butanamide, N-(4-cyclohexylphenyl)-4-(1,5-didesoxy-1,5-imino-D-glucit-N-yl)butanamide, 1-[3-(1,5-didesoxy-1,5-imino-D-glucit-N-yl)propionyl]-1,2,3,4-tetrahydroquinoline.

5. An antiviral composition comprising an antivirally effective amount of one or more compounds according to claim 1 and a pharmaceutically suitable excipient.

6. An antiviral composition according to claim 5 in dosage unit form.

7. A method of combating viral infections comprising administering to a patient having a viral infection an antiviral effective amount of one or more compounds according to claim 1.

8. A method according to claim 7 wherein the viral infection is an infection of a DNA virus or an RNA virus.

9. A method for the treatment and prophylaxis of diseases produced by retroviruses comprising administering to a patient in need of such treatment or prophylaxis an effective amount therefor of one or more compounds according to claim 1.

* * * * *

UNITED STATES PATENT AND TRADEMARK OFFICE
CERTIFICATE OF CORRECTION

PATENT NO. : 4,940,705

DATED : July 10, 1990

INVENTOR(S) : Boshagen et al.

It is certified that error appears in the above-identified patent and that said Letters Patent is hereby corrected as shown below:

Col. 60, claim 3 lines 58-59   After " tetrahydroisoquinoline " insert -- or --

Col. 61, claim 4 line 48   Delete " glusit " and substitute -- glucit --

Signed and Sealed this

Twenty-eighth Day of July, 1992

Attest:

DOUGLAS B. COMER

Attesting Officer    Acting Commissioner of Patents and Trademarks